(12) United States Patent
Uckun et al.

(10) Patent No.: US 11,649,232 B2
(45) Date of Patent: May 16, 2023

(54) SYNTHETIC DIMERIC CINCHONA ALKALOIDS AGAINST CANCER

(71) Applicant: Ares Pharmaceuticals, LLC, White Bear Lake, MN (US)

(72) Inventors: Fatih M. Uckun, White Bear Lake, MN (US); Taracad Venkatachalam, Mississagua, CA (US)

(73) Assignee: ARES PHARMACEUTICALS, LLC, White Bear Lake, MN (US)

( * ) Notice: Subject to any disclaimer, the term of this patent is extended or adjusted under 35 U.S.C. 154(b) by 58 days.

(21) Appl. No.: 17/316,005

(22) Filed: May 10, 2021

(65) Prior Publication Data
US 2022/0372029 A1 Nov. 24, 2022

(51) Int. Cl.
*C07D 453/04* (2006.01)
*A61P 35/00* (2006.01)

(52) U.S. Cl.
CPC ............ *C07D 453/04* (2013.01); *A61P 35/00* (2018.01)

(58) Field of Classification Search
CPC ............................... C07D 453/04; A61P 35/00
See application file for complete search history.

(56) References Cited

U.S. PATENT DOCUMENTS

| 4,716,171 | A | * | 12/1987 | Jarreau | ................ | C07D 453/04 |
| | | | | | | 546/136 |
| 5,635,515 | A | | 6/1997 | Chauffert et al. | | |
| 6,528,524 | B2 | | 3/2003 | Genne et al. | | |
| 9,301,956 | B2 | | 4/2016 | Celewicz et al. | | |
| 11,066,421 | B1 | * | 7/2021 | Uckun | ................... | A61P 35/04 |
| 2005/0112199 | A1 | | 5/2005 | Padval et al. | | |

FOREIGN PATENT DOCUMENTS

| CA | 2891633 A1 | 3/2015 |
| EP | 1477488 A1 | 11/2004 |
| PL | 215451 B1 | 5/2012 |

OTHER PUBLICATIONS

National Center for Biotechnology Information. PubChem Substance Record for SID 376752902, SID 376752902, Deposit Date Nov. 30, 2018, Source: Thieme Chemistry, https://pubchem.ncbi.nlm.nih.gov/substance/376752902. (Year: 2018).*
Uckun; PNAS 2010, 107, 2902-2907, with Supporting Information. 15 Pages, https://doi.org/10.1073/pnas.0909086107 (Year: 2010 ).*
Bodkin, J. A. and McLeod, M. D. "The Sharpless asymmetric aminohydroxylation" (2002) J. Chem Soc., Perkin Trans. 1, 2733-2746.
Boratyński, P. J. "Dimeric Cinchona alkaloids" (2015) Mol Divers 19: 385-422.
Brown, R. T. and Curiess, D. "Stereospecific Synthesis of Erythro Cinchona Alkaloids From Secologanin" (1986) Tetrahedron Letters 27(49): 6005-6008.
Chavez, K. J. et al. "Triple Negative Breast Cancer Cell Lines: One Tool in the Search for Better Treatment of Triple Negative Breast Cancer" (2010) Breast Dis. 32(1-2): 35-48.
Chemler, S. R. "Phenanthroindolizidines and Phenanthroquinolizidines: Promising Alkaloids for Anti-Cancer Therapy" (2009) Curr Bioact Compd. 5(1): 2-19.
Cuendet, M. and Pezzuto, .M. "Antitumor Alkaloids in Clinical Use or in Clinical Trials" (2007) Modern Alkaloids Structure, Isolation, Synthesis and Biology, 25-52.
Global Burden of Disease Cancer Collaboration "Global, Regional, and National Cancer Incidence, Mortality, Years of Life Lost, Years Lived With Disability, and Disability-Adjusted Life-Years for 29 Cancer Groups, 1990 to 2017" (2019) JAMA Oncol. 5(12): 1749-1768.
Rosenkranz, V. and Wink, M. "Alkaloids Induce Programmed Cell Death in Bloodstream Forms of Trypanosomes (Trypanosoma b. brucei)" (2008) Molecules 13: 2462-2473.
Kolb, H. C. et al. "Catalytic Asymmetric Dihydroxylation" (1994) Chem. Rev. 94: 2483-2547.
Lee, A. and Lee, F. C. "Medical oncology management of advanced hepatocellular carcinoma 2019: a reality check" (2020) Front. Med. 14(3): 273-283.
Lee, S. Y. et al. "Hydrocinchonine, Cinchonine, and Quinidine Potentiate Paclitaxel-Induced Cytotoxicity and Apoptosis via Multidrug Resistance Reversal in MES-SA/DX5 Uterine Sarcoma Cells" (2011) Environ Toxicol. 26(4): 424-431.
Martirosyan, A. R. et al. "Differentiation-inducing quinolines as experimental breast cancer agents in the MCF-7 human breast cancer cell model" (2004) Biochemical Pharmacology 68(9):1729-1738.
Myers, D. E. et al. "CD19-antigen specific nanoscale liposomal formulation of a SYK P-site inhibitor causes apoptotic destruction of human B-precursor leukemia cells" (2014) Integr Biol (Camb). 6(8): 766-780.
Rafei, H. et al. "Targeted therapy paves the way for the cure of acute lymphoblastic leukaemia" (2020) British Journal of Haematology 188: 207-223.
Vaddepally, R. K. et al. "Review of Indications of FDA-Approved Immune Checkpoint Inhibitors per NCCN Guidelines with the Level of Evidence" (2020) Cancers 12: 738(1-19).
Rosenkranz, V. and Wink, M. "Induction of Apoptosis by Alkaloids, Non-Protein Amino Acids, and Cardiac Glycosides n Human Promyelotic HL-60 Cells" (2007) Z Naturforsch C J Biosci. 62: 458-466.

(Continued)

*Primary Examiner* — Daniel R Carcanague
(74) *Attorney, Agent, or Firm* — Volpe Koenig

(57) ABSTRACT

Synthetic, novel dimeric cinchona alkaloid compounds having potent cytotoxic activity against human cancer cells. The compounds are effective agents for inhibiting cellular proliferation, for example, in cancer cells. The compounds cause apoptotic cell death in and cause inhibition of clonogenic growth of human breast cancer, prostate cancer, leukemia, lymphoma cells at nanomolar concentrations. The chemical structure of the compound includes dimeric cinchona alkaloid and derivatives containing various groups attached in their structure. The compounds also possess hydroxy group functionality in the structure to enable the preparation of pharmaceutically applicable salts to enhance their solubility for ease of systemic administration in animals and in humans, for example, in cancer patients.

10 Claims, 7 Drawing Sheets

(56) References Cited

OTHER PUBLICATIONS

Sahin, T. K. et al. "Anti-prostate cancer activity of a nanoformulation of the spleen tyrosine kinase (SYK) inhibitor C61" (2020) Anti-Cancer Drugs 31(6): 609-616.

Solary, E. et al. "Phase I study of cinchonine, a multidrug resistance reversing agent, combined with the CHVP regimen in relapsed and refractory lymphoproliferative syndromes" (2000) Leukemia 14: 2085-2094.

Tao, H. et al. "Alkaloids as Anticancer Agents: A Review of Chinese Patents in Recent 5 Years" (2020) Recent Patents on Anti-Cancer Drug Discovery 15: 2-13.

Uckun, F. M. et al. "STAT3 is a substrate of SYK tyrosine kinase in B-lineage leukemia/lymphoma cells exposed to oxidative stress" (2010) PNAS 107(7): 2902-2907.

Uckun, F. M. et al. "Targeting SYK kinase-dependent anti-apoptotic resistance pathway in B-lineage acute lymphoblastic leukaemia (ALL) cells with a potent SYK inhibitory pentapeptide mimic" (2010) British Journal of Haematology 149: 508-517.

Uckun, F. M. et al. "Nanoscale liposomal formulation of a SYK P-site inhibitor against B-precursor leukemia" (2013) Blood 121(21): 4348-4354.

Uckun, F. M. et al. "Liposomal Nanoparticles of a Spleen Tyrosine Kinase P-Site Inhibitor Amplify the Potency of Low Dose Total Body Irradiation Against Aggressive B-Precursor Leukemia and Yield Superior Survival Outcomes in Mice" (2015) EBioMedicine 2(6): 554-562.

Uckun, F. M. et al. "Inducing apoptosis in chemotherapy-resistant B-lineage acute lymphoblastic leukaemia cells by targeting HSPA5, a master regulator of the anti-apoptotic unfolded protein response signalling network" (2011) British Journal of Haematology 153(6):741-752.

Uckun, F. M. et al. "Recombinant human CD19L-sTRAIL effectively targets B cell precursor acute lymphoblastic leukemia" (2015) J Clin Invest. 125(3): 1006-1018.

Uckun, F. M et al. "Contemporary patient-tailored treatment strategies against high risk and relapsed or refractory multiple myeloma" (2019) EBioMedicine. 39: 612-620.

Uckun, F. M et al. "Recurrent or Refractory High-Grade Gliomas Treated by Convection-Enhanced Delivery of a TGFβ2-Targeting RNA Therapeutic: A Post-Hoc Analysis with Long-Term Follow-Up" (2019) Cancers (Basel) 11(12): 1892 (1-21).

Marla, R. K. et al. "4-(3' -Bromo4' hydroxylphenyl)-amino-6,7-dimethoxyquinazoline: A Novel Quinazoline Derivative with Potent Cytotoxic Activity against Human Glioblastoma Cells" (1998) Clinical Cancer Research 4: 1405-1414.

Uckun, F. M. et al. "CD22 Exon 12 deletion as a pathogenic mechanism of human B-precursor leukemia" (2010) PNAS 107(39): 16852-16857.

Uckun, F. M. et al. "Serine phosphorylation by SYK is critical for nuclear localization and transcription factor function of karos" (2012) PNAS 109(44): 18072-18077.

Uckun, F. M. et al. "Vinorelbine-based salvage chemotherapy for therapy-refractory aggressive leukaemias" (2006) Br J Haematol 135(4): 500-508.

Narla, R. K. et al. "In Vivo Antitumor Activity of Bis(4,7-dimethyl-1,10-phenanthroline) Sulfatooxovanadium(IV) {METVAN [VO(SO4)(Me2-Phen)2]}" (2001) Clinical Cancer Research 7: 2124-2133.

Li, H. Y. et al. "The Tumor Microenvironment Regulates Sensitivity of Murine Lung Tumors to PD-1/PD-L1 Antibody Blockade" (2017) Cancer Immunol Res 5(9): 767-777.

Deskin, B. et al. "Inhibition of HDAC6 Attenuates Tumor Growth of Non-Small Cell Lung Cancer" (2020) Translational Oncology 13(2): 135-145.

Dibirdik, I. et al. "In vivo Anti-Cancer Activity of a Liposomal Nanoparticle Construct of Multifunctional Tyrosine Kinase Inhibitor 4-(4'-Hydroxyphenyl)-Amino-6,7-Dimethoxyquinazoline" (2010) J Nanomedic Nanotechnolo 1: 101 (2-4).

Uckun, F. M. et al. "Anti-breast cancer activity of LFM-A13, a potent inhibitor of Polo-like kinase (PLK)" (2007) Bioorganic & Medicinal Chemistry 15: 800-814.

Kellar, A. et al. "Preclinical Murine Models for Lung Cancer: Clinical Trial Applications" (2015) Biomed Res Int. 2015: 621324 (1-17).

Richmond, A. and Su, Y. "Mouse xenograft models vs GEM models for human cancer therapeutics" (2008) Disease Models & Mechanisms 1: 78-82.

Xu, C. et al. "Patient-derived xenograft mouse models: A high fidelity tool for individualized medicine (Review)" (2019) Oncology Letters 17: 3-10.

Siva, A. and Murugan, E. et al. "A New Trimeric Cinchona Alkaloid as a Chiral Phase-Transfer Catalyst for the Synthesis of Asymmetric a-Amino Acids" (2005) Synthesis 17: 2927-2933.

Park, H. G. et al. "Trimeric Cinchona alkaloid phase-transfer catalyst: αα',α''-tris[O(9)-allylcinchonidinium]mesitylene tribromide" (2001) Tetrahedron Letters 42: 4645-4648.

Takata, S. et al. "Synthesis of cinchona alkaloid sulfonamide polymers as sustainable catalysts for the enantioselective desymmetrization of cyclic anhydrides" (2016) RSC Adv. 6: 72300-72305.

Parvez, M. et al. "Synthesis of Cinchona Alkaloid-Derived Chiral Polymers by Mizoroki-Heck Polymerization and Their Application to Asymmetric Catalysis" (2014) Macromolecules 47: 1922-1928.

Marcelli, T. "Cinchona-derived organocatalysts for asymmetric carbon-carbon bond formation" (2007) Thesis, University of Amsterdam.

Ihara M. et al. "Total synthesis of hydrocinchonidine and hydrocinchonine via photo-oxygenation of an indole derivative", (1988) Chem. Soc. Perkin Trans. I: 1277-1281.

Mattock, N.M. and Peters, W. "The experimental Chemotherapy of leishmaniasis, III Detection of antileishmanial activity in some new synthetic compounds in a tissue culture model" (1975) Annals of Tropical Medicine and Parasitology 69(4): 449-462.

Schlager, S. and Drager, B. "Exploiting plant alkaloids" (2016) Curr Opin Biotechnol 37:155-164.

Uckun, F. M. et al. "Use of a novel colony assay to evaluate the cytotoxicity of an immunotoxin containing pokeweed antiviral protein against blast progenitor cells freshly obtained from patients with common B-lineage acute lymphoblastic leukemia" (1986) J. Exp. Med.163: 347-368.

Uckun, F. M. et al. "Intrinsic radiation resistance of primary clonogenic blasts from children with newly diagnosed B-cell precursor acute lymphoblastic leukemia" (1993) J. Clin. Invest. 91:1044-1051.

\* cited by examiner

SYNTHETIC DIMERIC CINCHONA ALKALOIDS AGAINST CANCER

FIELD

The invention relates to novel synthetic dimeric cinchona alkaloid compounds as potent anti-cancer agents.

BACKGROUND

Cancer is a major disease that continues as one of the leading causes of death at any age (Fitzmaurice, C. et al., 2019, *JAMA Oncol.*, 5:1749-1768). There is an urgent need for the development and analysis of novel, effective anticancer agents. Considerable efforts are underway to develop new chemotherapeutic agents for more potent and specific anti-cancer therapy, presenting effective and efficient cytotoxicity against tumor cells, with minimal interference with normal cell function (Rafei, H. et al., 2020, Br J. Haematol., 188: 207-223; Lee, A., Lee, F-C, 2020, Front Med. 14: 273-283; Vaddepaly, R. K. et al., 2020, Cancers 12: 738; Uckun, F. M. et al., EBioMedicine 39:612-620). Cancer is associated with higher morbidity and mortality and is the second leading cause of death in the US. In 2017, there were 24.5 million incident cancer cases worldwide and 9.6 million cancer deaths (Fitzmaurice, C. et al., 2019, *JAMA Oncol.*, 5:1749-1768). The most common causes of cancer deaths for men were tracheal, bronchus, and lung (TBL) cancer (1.3 million deaths and 1.5 million incident cases), liver cancer (572 000 deaths), and stomach cancer (542 000 deaths). The leading cause of cancer deaths for women was breast cancer (601 000 deaths), which was the second most incident cancer (1.9 million incident cases).

B-lineage acute lymphoblastic leukemia (B-ALL) is the most common form of cancer in children and adolescents (1-3). A number of new therapies have been approved by the US Food and Drug Administration in the past 5 years, including blinatumomab in 2014, inotuzumab ozagamicin in 2017 and tisagenlecleucel in 2017 for relapsed/refractory ALL. This has led to tremendous improvement in long-term survival, of more than 50% in patients with precursor B-ALL [50-70% in patients with Philadelphia chromosome (Ph)-positive ALL)], 50-60% in T-ALL and 80% in mature B-ALL. Research is ongoing to optimize the benefit of targeted therapeutics with the goal of decreasing the use of cytotoxic therapies (Rafei, H. et al., 2020, Br J. Haematol., 188: 207-223).

Currently, the major challenge in the treatment of B-ALL is to cure patients who have relapsed despite intensive frontline chemotherapy (Uckun, F. M. et al., 2011, Br. J. Haematol., 153:741-752; Uckun, F. M., 2015, J Clin Invest., 125:1006-18). Chemotherapy resistance at relapse is a major obstacle to the success of contemporary "salvage" regimens, since only a minority of relapsed BPL patients become long-term disease-free survivors even after very intensive radiochemotherapy in the context of hematopoietic stem cell transplantation. There is an urgent and unmet need to identify new drug candidates capable of destroying chemotherapy-resistant B-ALL cells. Likewise, patients with relapsed T-lineage ALL (T-ALL) have less than 25% event-free and overall survival rates on contemporary treatments. Prostate cancer, the most common type of cancer among men, is the second leading cause of cancer-related deaths (Fitzmaurice, C. et al., 2019, JAMA Oncol., 5:1749-1768). Advanced prostate cancer has a dismal outcome and patients with metastatic disease are in urgent need for therapeutic innovations. Treatment of androgen deprivation by both chemical and surgical castration is initially useful in the treatment of metastatic prostate cancer (PC), but patients ultimately enter to the metastatic, castration-resistant stage, mCRPC, where there is no an effective treatment. Likewise, advanced and metastatic breast cancer patients, especially those with triple-negative breast cancer (TNBC) are in urgent need for therapeutic innovations (Chavez, K. J., et al., 2010, Breast Dis., 32: 35-48). The prognosis of high-grade gliomas (HGG) has not significantly improved despite recent advances in neurosurgery, chemotherapy, immune-oncology, and radiation therapy (Uckun, F. M., et al., 2019, Cancers (Basel) 2019; 11(12). pii: E1892. doi: 10.3390/cancers11121892). The average overall survival of patients with glioblastoma multiforme (GBM) is merely 10-12 months. Most patients experience the recurrence or progression of their disease within 12 months after frontline therapy and face a dismal outcome with no effective therapy. Therefore, effective salvage therapies are needed for recurrent/refractory HGG patients who have failed their first line standard therapy. Since the FDA approval of ipilimumab (human IgG1 k anti-CTLA-4 monoclonal antibody) in 2011, six more immune checkpoint inhibitors (ICIs) have been approved for cancer therapy. PD-1 inhibitors nivolumab, pembrolizumab, cemiplimab and PD-L1 inhibitors atezolizumab, avelumab, and durvalumab are in the current list of the approved agents in addition to ipilimumab (Vaddepaly, R. K. et al., 2020, Cancers 12: 738). In terms of global cancer-related deaths, hepatocellular carcinoma (HCC) has the fourth highest mortality rate (Fitzmaurice, C. et al., 2019, *JAMA Oncol.*, 5:1749-1768). Up until 2017, treatment of advanced HCC was largely limited to sorafenib, an oral tyrosine kinase inhibitor, with little to no success in the development of alternative treatment options. However, in the past two years, there has been an unprecedented increase in both the number and type of treatment options available for HCC. As of 2019, the US FDA has approved four oral tyrosine kinase inhibitors, two immune checkpoint inhibitors, and one anti-angiogenesis antibody for the treatment of HCC. Even with this new variety, systemic treatment of advanced HCC remains largely unsatisfactory, and the median survival rate stands at approximately one year (Lee, A., Lee, F-C, 2020, Front Med. 14: 273-283). The expected breakthrough of using immune checkpoint inhibitors in advanced HCC did not materialize in 2019. The use of immune checkpoint inhibitors in conjunction with oral tyrosine kinase inhibitors or anti-angiogenesis medications is the current clinical research trend, the results of which are eagerly anticipated.

The bark of various Cinchona species contains 4 major quinoline alkaloids, namely quinine (QN), quinidine (QD), cinchonidine (CD), and cinchonine (CN) (Boratynski, P. J., 2015, Mol Divers, 19:385-422; Brown, R. T. and Curless, D., Tetrahedron Letters., 1986, 27: 6005-6008; Ihara, M. et al., J. Chem. Soc. Perkin Trans., 1988, 1, 1277-1281; Mattock, M. M. and Peters, P. Annals of Tropical Medicine and Parasitology, 1975, 69:, 449-462). Cinchona alkaloids have been used in organic chemistry to catalyze chemical reactions (Kolb, H. C. et al., Chem. Rev., 1994, 94, 2483-2547; Baldwin, J. A., McLeod, M. D., J. Chem Soc. Perkin Trans. 2002, 1: 2733-2746). It has been known that many of the alkaloids affect a broad spectrum of cellular targets and metabolic pathways leading to cytotoxicity (Schläger, S., Dräger, B., Curr Opin Biotechnol., 2016, 37: 155-64; Chemler, S. R., Curr Bioact Compd., 2009, 5: 2-19; Tao, H. et al., Recent Patents on Anticancer Drug Discovery, 2020, 15: 2-13; Cuendet M, Pezuto J M. [In] Modern Alkaloids: Structure, Isolation, Synthesis and Biology; 2007; pp.

25-52). Rosenkranz et al (Rosenkranz, V., Winke, M, Molecules 2008, 13, 2462-2473) reported the influence of alkaloids on the programmed cell death in blood stream forms of trypanosomes. They concluded that the pro-apoptotic activity of these alkaloids is related to the inhibition of protein synthesis, to intercalate DNA, to disturb membrane fluidity or to inhibit microtubule formation. They also reported that alkaloids induce apoptosis in a human promyelocytic leukemia cell line (Rosenkranz, V., Winke, M. Z. Naturforsch., 2007, 62c: 458-466).

Hydrochinconine, cinchonine and quinidine have been shown to reverse multi-drug resistane and enhance chemotherapy sensitivity of human cancer cells (Solary, E., et al., Leukemia, 2000, 14, 2085-2094; Lee, S. Y. et al., Environmental Toxicology, 201, 26: 424-431). Other studies have shown that quinolones can cause terminal differentiation of undifferentiated cancer cells (AR Martirosyan, A. R. et al., Biochemical Pharmacology, 2004, 68, 1729-1738). The stereoisomers QN and QD as well as their reduced forms, dihydroquinidine (DHQD) and dihydroquinine (DHQ) are naturally occurring cinchona alkaloids that lack anti-cancer activity (Uckun, F. M. et al., *Proc. Natl. Acad. Sci. USA* 2010, 107: 2902-2007). The modification of these cinchona alkaloids at their $C_9$—OH moiety yielded derivatives with varying levels of cytotoxic activity against human cancer cells. Uckun et al. recently reported a C2-symmetric cinchona alkaloid derivative, 1,4-Bis (9-O dihydroquinidinyl) phthalazine/hydroquinidine 1,4-phathalazinediyl diether (C-61) as a first-in-class anti-leukemic compound capable of inhibiting the anti-apoptotic SYK-STAT3 signaling in leukemia cells (Uckun, F. M. et al., *Proc. Natl. Acad. Sci. USA* 2010, 107(7): 2902-7; Uckun, F. M. et al., *British Journal of Haematology* 2010, 149(4): 508-17). A liposomal nanoformulation of C61 exhibited potent anti-leukemic activity both in vitro and in vivo (Uckun, F. M. et al., Blood. 2013, 121:4348-54; Myers, D. E. et al., *Integr Biol (Camb)*. 2014, 6:766-80; Uckun, F. M. et al., EBioMedicine. 2015, 2:554-62). The identification of novel cinchona alkaloids with potent cytotoxicity against TNBC, CRPC, GBM, and ALL cells may through lead optimization and translational research lead to the development of a new class of potent new anti-cancer agents for difficult to treat forms of cancer.

SUMMARY

In an aspect, the invention relates to a compound of Formula I, Compound A, Formula II, Compound B, Formula III, a hydroxy-substituted cinchona alkaloid of Formula III, a prodrug of the compound of Formula I, Compound A, Formula II, Compound B, Formula III, or a hydroxy-substituted cinchona alkaloid of Formula III:

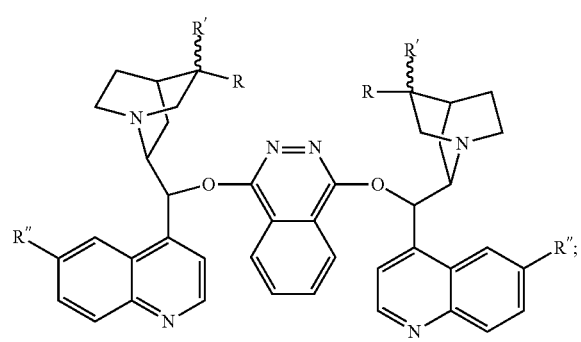

I

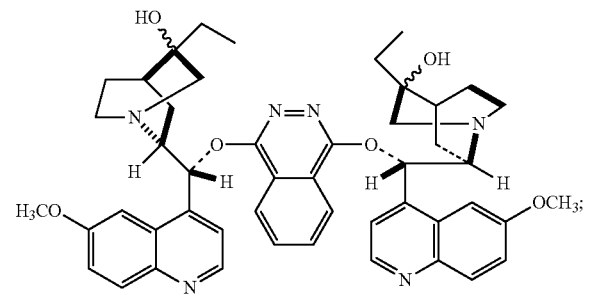

Compound A

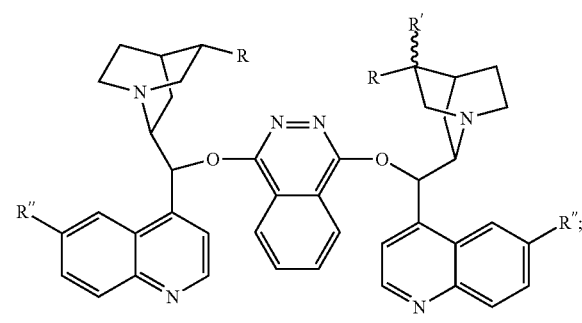

II

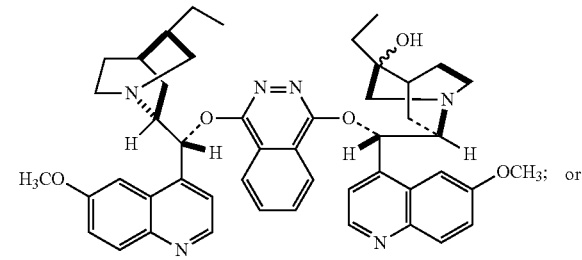

Compound B

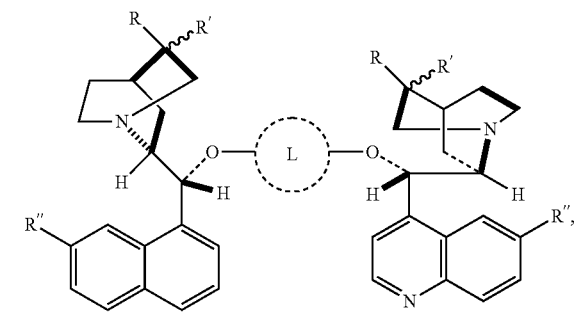

III

For the compound of Formula I, R is, independent of R' and R", selected from the group consisting of H, Me, Et, Pr, Bu, tBu, Ph,PhCH$_2$, OH, OMe, OEt, OPr, OBu,OtBu, OPh, OCH$_2$Ph. R' is, independent of R and R", selected from the group consisting of OH, OMe, OEt, OPr, OBu, OtBu, OPh, or OCH$_2$Ph. R" is, independent of R and R', selected from the group consisting of OMe, OEt, OPh, F, Cl, Br, I, COOH, COOMe, or COOEt. The alkaloid moiety may be chosen independently from any one of Cinchonidine, Quinine, Cinchonine, Quinidine, or any substituted heterocyclic as shown above for Formulas I, II, or III and Compound A or Compound B, or a pharmaceutically acceptable salt thereof. Compound A is (2-[6-({4-({5-ethyl-5-hydroxy-1-azabicyclo [2.2.2]octan-2-yl}(6-methoxyquinolin-4yl)methoxy)phthalazine-1-yl}oxy}(6-methoxyquinolin-4yl) methyl)-3hydroxy-1-azabicyclo[2.2.2]octan-3yl]ethylidyne). For the compound of formula II, R, R' and R" can be the same or different. R is, independent of R' and R", selected from the group consisting of H, Me, Et, Pr, Bu, tBu, Ph,PhCH$_2$, OH, OMe, OEt, OPr, OBu,OtBu, OPh, or OCH$_2$Ph. R' is, independent of R and R", selected from the group consisting of OH, OMe, OEt, OPr, OBu, OtBu, OPh, or OCH$_2$Ph. R" is, independent of R or R', selected from the group consisting of OMe, OEt, OPh, F, Cl, Br, I, COOH, COOMe, or COOEt. The alkaloid moiety may be chosen independently from any one of the following compounds, or a substituted heterocyclic derivative or a pharmaceutically acceptable salt thereof: Cinchonidine, Quinine, Cinchonine, Quinidine. Compound B is (2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl) methyl)-1-azabicyclo[2.2.2]octan-3-yl] ethylidyne). For the compound of Formula III, the linker moiety L represents 1,4-dichlorophthalazine, 1,4-dicholoroanthraquinone or 3,6-dichloropyridazine and their derivatives and (i) moieties that contain bicyclic, tricyclic, or tetracyclic ring attached heterocycles, 1,4-dichlorophthalazine; 2,4-dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-cloro-3,6-dibromopyrimidine; 3,6-dichloro-4-methyl pyridazine; 2,6-difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; or 2,4-dichloropyrimidine, or (ii) molecules that contain hetero atoms, N, O,S, Se, Te; or (iii) molecules that contain halogen atoms, F,Cl,Br, or I. For the hydroxy-substituted cinchona alkaloid compound of Formula III, the linker moiety L represents 1,4-dichlorophthalazine, 1,4-dicholoroanthraquinone or 3,6-dichloropyridazine and their derivatives or may be chosen independently from any one of the following compounds 1,4-dichlorophthalazine; 2,4-dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-cloro-3,6-dibromopyrimidine; 3,6-dichloro-4-methyl pyridazine; 2,6-difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; or 2,4-dichloropyrimidine; a substituted heterocyclic derivative or one of:

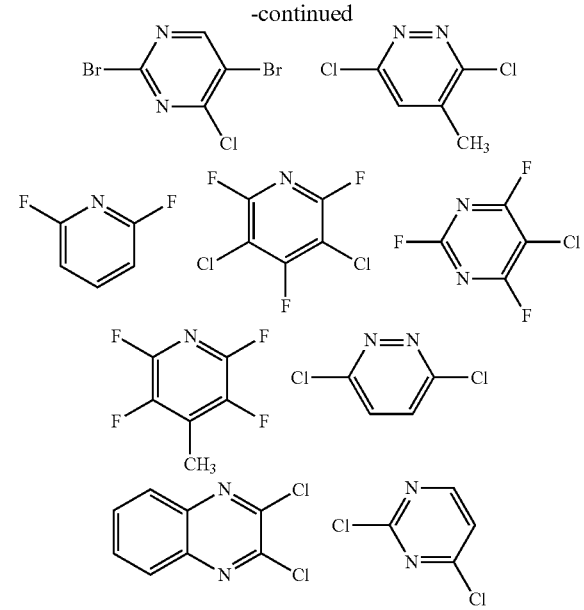

The compound may be pharmaceutically acceptable salt of any of the foregoing.

In an aspect, the invention relates to a pharmaceutical composition comprising any compound of the preceding paragraph. The pharmaceutical composition may comprise a pharmaceutically acceptable carrier.

In an aspect, the invention relates to a method for treating cancer in a mammal comprising administering to the mammal in need of said treatment an effective amount of the compound of the above paragraph starting with "In an aspect, the invention relates to a compound", a pharmaceutically acceptable salt thereof, or a pharmaceutical composition thereof. The compound may be the compound of Formula I, Formula II, Formula III, or Compound A or Compound B; or a pharmaceutically acceptable salt thereof, or a pharmaceutical composition thereof.

In an aspect, the invention relates to a method for inducing apoptosis of cancer cells comprising contacting the cancer cells with an effective apoptosis-inducing amount the compound of the above paragraph starting with "In an aspect, the invention relates to a compound", a pharmaceutically acceptable salt thereof, or a pharmaceutical composition thereof.

In an aspect, the invention relates to a method for inhibiting the growth of cancer cells comprising contacting the cells with an effective inhibitory dose of the compound of the above paragraph starting with "In an aspect, the invention relates to a compound", a pharmaceutically acceptable salt thereof, or a pharmaceutical composition thereof.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION

Figure 1:
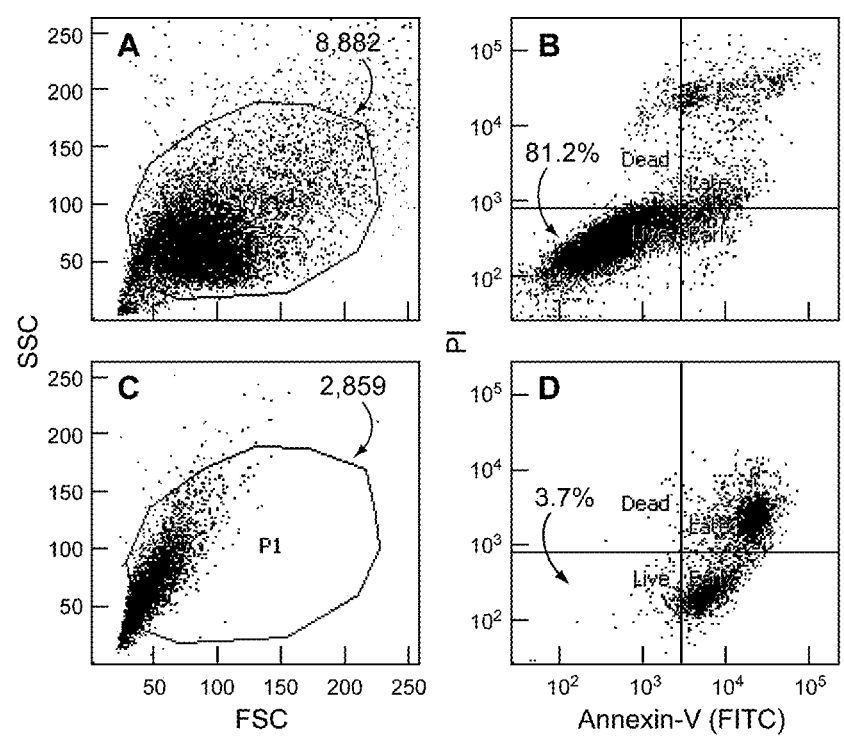
FIG. 1 shows the flow cytometric evidence for the ability of Compound A ("ARES-BI-C001453") to cause apoptotic destruction of human T-lineage ALL cell line, LOUCY. After ARES-BI-C001453 treatment, LOUCY cells exhibited marked shrinkage, with altered side scatter (SSC) as well as decreasing numbers of remaining cells in the P1 lymphoid window in the corresponding forward scatter (FSC)/SSC light scatter plot from the 10,000 cells analyzed (A versus C). The anti-leukemic potency of ARES-BI-C001453 against leukemia cells was further evidenced by the significantly lower percentages of Annexin V-FITC$^-$ PI$^-$ live cells located in the left lower quadrant of the corresponding two-color FACS histogram as well as substantially higher percentage of Annexin V-FITC$^+$ PI$^+$ apoptotic cells located in the right upper quadrant (B versus D).

Certain terminology is used in the following description for convenience only and is not limiting. The words "right," "left," "top," and "bottom" designate directions in the drawings to which reference is made.

All scientific and technical terms used in this application have meanings commonly used in the art unless otherwise specified. As used in this application, the following words or phrases will have the meanings:

As used herein, "pharmaceutically acceptable salt or carrier" includes any material which, when combined with a compound of the invention, allows the compound to retain biological activity, such as the ability to induce apoptosis of cancer cells. Examples include, but not limited to, any of the standard pharmaceutical carriers, such as a phosphate buffered saline solution, water, emulsions such as oil/water emulsions, and various types of wetting agents. Also included are PEG'ylation, and liposome systems as useful carriers of the compositions of the invention. In addition, carrier molecules such as specific anti-cancer antigen antibodies and ligands such as epidermal growth factor (EGF) can be used to carry the compound to the target cells. Compositions comprising such carriers, including composite molecules, are formulated by well known conventional methods (see for example, Remington's Pharmaceutical Sciences, Chapter 43, 14$^{th}$ Ed., Mack Publishing Co., Easton, Pa.).

"Treating", Treatment or "to treat" in the context of this invention means to inhibit or block at least one symptom that characterizes a pathologic condition., in a mammal threatened by, or afflicted with, the condition. In context of cancer therapy, treatments include induction of tumor cell death, and increased programmed cell death, also known as apoptosis. Treatment also includes the prevention of cancer cell adhesion and migration into tissues which may lead to metastatic spread of cancer to multiple organs. "Inhibit" means to reduce by a measurable amount, or to prevent entirely.

"Multi-Drug Resistant Cancer Cells" means one or more type of cancer cell which is resistant to treatment with one or more chemotherapeutic agent. "Therapeutically effective amount" is a dose which provides some therapeutic benefit on administration, including in the context of the invention, inhibition of cancer cell growth and/or proliferation, prevention or inhibition of apoptosis, reduction in tumor mass, prevention of cancer cell adhesion and/or migration; and increase in patient longevity.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

We are now reporting the discovery, synthesis and anti-cancer cell activity of 2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl)methyl)-3hydroxy-1-azabicyclo[2.2.2]octan-3yl]eth ylidyne (ARES-BI-C0001453) which was identified as a novel compound with broad-spectrum activity against human cancer cell lines derived from triple-negative breast cancer (TNBC), castration-resistant prostate cancer (CRPC), glioblastoma (GBM), and acute lymphoblastic leukemia (ALL) patients as well as in vivo clonogenic leukemia-initiating cells capable of causing disseminated and invariably fatal leukemia in a NOD-SCID mouse xenograft model of ALL.

The identification of ARES-BI-C0001453 as a novel chemical entity (NCE) with potent cytotoxicity against TNBC, CRPC, GBM, and ALL cells may through lead optimization and translational research lead to the development of a new class of potent new anti-cancer agents for difficult to treat forms of cancer. The potent activity of ARES-BI-C0001453 against the CRPC cell line PC-3, TNBC cell line BT-20, GBM cell line U373, ALL cell lines ALL-1 and Loucy, high-grade lymphoma cell line RAJI warrants its further development and evaluation of its clinical potential as a new broad-spectrum anti-cancer drug candidate.

Furthermore, Cinchona alkaloids as well as their polymers can be used as catalysts of complex chemical reactions in organic chemistry, for example for the enantioselective desymmetrization of cyclic anhydrides, asymmetric synthesis of amino acids (Ayyanar Siva, Eagambaram Murugan. Synthesis 2005; 17:2927-2933; Hyeung-geun Park et al. Tetrahedron Letters, Volume 42, Issue 28, 2001, Pages 4645-4648; Shohei Takata et al., RSC Adv., 2016, 6, 72300-72305; Masud Parvez et al., Macromolecules 2014, 47, 6, 1922-1928; Marcelli, T. 2007, UvA-DARE (Digital Academic Repository).

Synthetic dimeric cinchona alkaloid compounds having the chemical structure (I, II, III, Compound A, Compound B) were synthesized and examined for their cytotoxic effects on cancer cells, including human leukemia, breast cancer, prostate cancer and brain cancer cells. Synthetic lead compounds Compound A and Compound B were found to exhibit potent cytotoxic activity against cancer cells at nanomolar concentrations.

Generally, the present invention relates to novel compounds and compositions having potent cytotoxic activity against cancer cells. One embodiment relates to compositions containing an effective cytotoxic or inhibitory amount of a synthetic cinchona alkaloid compound having the chemical structure (I, II, III, Compound A, Compound B). The cytotoxic compounds of the invention include those having the following formulae:

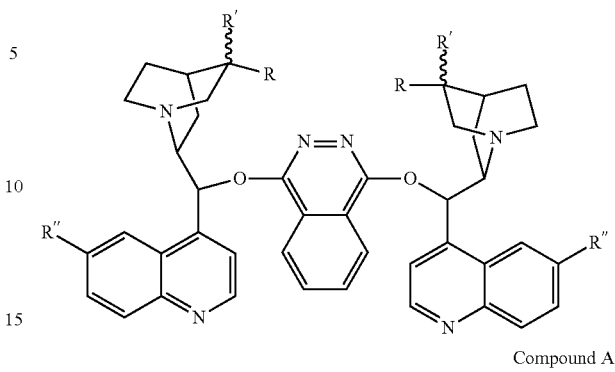

I

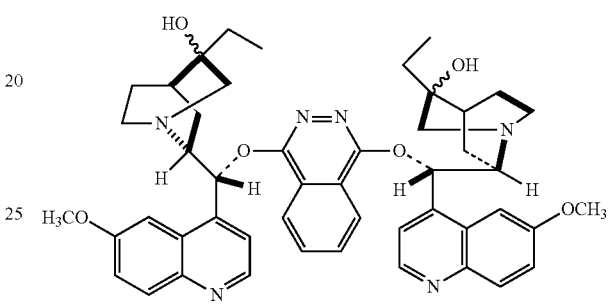

Compound A

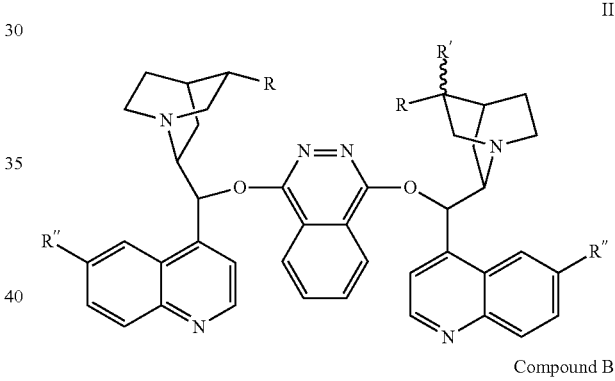

II

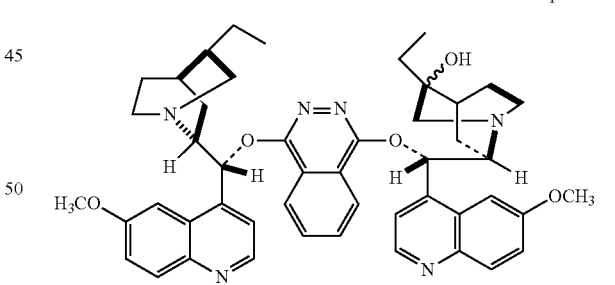

Compound B

Another embodiment of the present invention provides compositions formulated for delivery of the cytotoxic cinchona alkaloid compounds to a subject as a pharmaceutical composition. The compounds of the invention are combined with a suitable carrier to form compositions suitable for use in cancer therapy.

A further embodiment of the present invention provides methods to inhibit the growth or induce apoptosis of cancer cells, by administering to a subject or contacting cancer cells with an effective amount of a compound or composition of the present invention.

A further embodiment of the present invention provides a method for the synthesis of novel dimeric cinchona alkaloid derivatives as described in the Examples below.

Compounds

The invention provides a dimeric hydroxy-substituted cinchona alkaloid compound of Formula I, that can be synthesized by coupling two molecules of cinchona alkaloids to one molecule of linker such as 1,4-dichlorophthalazine, 1,4-dicholoroanthraquinone or 3,6-dichloropyridazine. The compounds of the invention have the general structure shown in Formula I, wherein R is, independent of R' and R", H, Me, Et, Pr, Bu, tBu, Ph,PhCH$_2$, OH, OMe, OEt, OPr, OBu,OtBu, OPh, OCH$_2$Ph; R' is, independent of R and R", OH, OMe, OEt, OPr, OBu, OtBu, OPh, or OCH$_2$Ph; and R" is, independent of R and R', OMe, OEt, OPh, F, Cl, Br, I, COOH, COOMe, or COOEt; (see abbreviation list) or a pharmaceutically acceptable salt thereof.

I

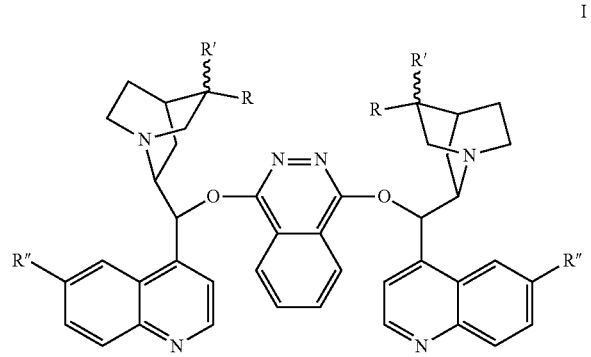

One preferred compound of the present invention is Compound A (2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl) methyl)-3hydroxy-1-azabicyclo[2.2.2]octan-3yl]ethylidyne) or a pharmaceutically acceptable salt thereof:

Compound A

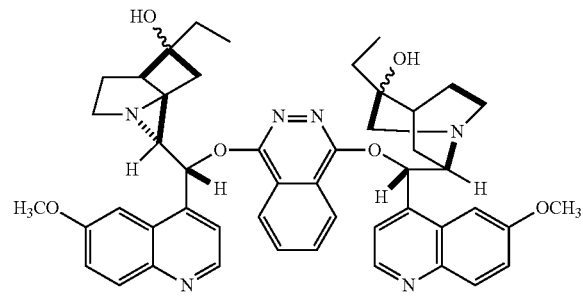

The invention also provides a compound of formula II that can be synthesized by coupling cinchona alkaloid molecules to one molecule of linker such as 1,4-dichlorophthalazine, 1,4-dicholoroanthraquinone or 3,6-dichloropyridazine, wherein R, R' and R"" can be the same or different; and R is, independent of R' and R", H, Me, Et, Pr, Bu, tBu, Ph,PhCH$_2$, OH, OMe, OEt, OPr, OBu,OtBu, OPh, or OCH$_2$Ph; R' is, independent of R and R", OH, OMe, OEt, OPr, OBu, OtBu, OPh, or OCH$_2$Ph; and R" is, independent of R or R', OMe, OEt, OPh, F, Cl, Br, I, COOH, COOMe, or COOEt; (see abbreviation list) or a pharmaceutically acceptable salt thereof.

II

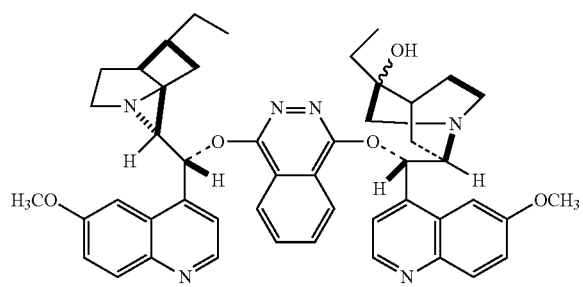

The invention in particular provides Compound B (2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl) methyl)-1-azabicyclo[2.2.2]octan-3-yl] ethylidyne) or a pharmaceutically acceptable salt thereof:

Compound B

The invention also provides compounds wherein the alkaloid moiety may be chosen independently from any one of Cinchonidine, Quinine, Cinchonine, Quinidine, or a substituted heterocyclic derivative as shown above for Formula I, II, or III and Compound A or Compound B, or a pharmaceutically acceptable salt thereof.

The invention also provides hydroxy-substituted cinchona alkaloid compounds of Formula III wherein the linker moiety L may be chosen independently from any one of the following non-limiting list exemplary compound: 1,4-dichlorophthalazine, 1,4-dicholoroanthraquinone or 3,6-dichloropyridazine and their derivatives (see linker list) and any appropriately substituted heterocyclic derivative or a pharmaceutically acceptable salt thereof "L" represents the linker moiety (see linker list) which may comprise of halo substituted heterocycles which may be but are not limited to the following examples: 1,4-dichlorophthalazine, 1,4-dicholoroanthraquinone or 3,6-dichloropyridazine and their derivatives. L may be one of the following:

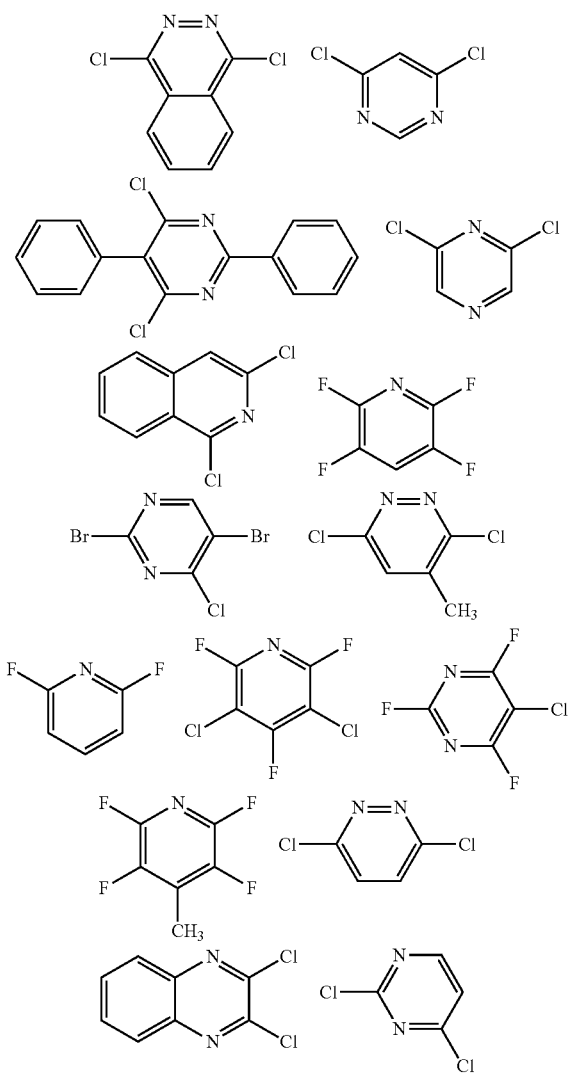

This invention also provides compounds of Formula III, wherein the linker moiety L may be but is not limited to 1,4-dichlorophthalazine, 1,4-dicholoroanthraquinone or 3,6-dichloropyridazine and their derivatives and (i) molecules that contain bicyclic, tricyclic and tetracyclic ring attached heterocycles or (ii) molecules that contain hetero atoms including but not limited to N, O, S, Se, Te; or (iii) molecules that contain halogen atoms including F, Cl, Br or I; or pharmaceutically acceptable salts thereof.

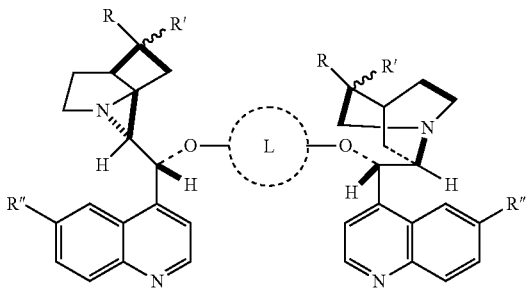

III

The invention also provides a pharmaceutical composition comprising a compound of Formula I, or a compound of Formula II or a compound of Formula III, or Compound A, or Compound B; and a pharmaceutically acceptable carrier, including but not limited to liposomes, fusion proteins, target-specific ligands or monoclonal antibodies.

The invention provides a method for treating cancer in a mammal comprising administering to the mammal in need of such treatment an effective amount of a compound in Formula I, Formula II, Formula III, or Compound A or Compound B; or a pharmaceutically acceptable salt thereof, or a pharmaceutical composition thereof The invention provides a method for treating a human cancer patient, especially a patient with breast cancer, prostate cancer, glioblastoma multiforme, leukemia, or lymphoma with an effective amount of a compound in Formula I, Formula II, Formula III, or Compound A or Compound B; or a pharmaceutically acceptable salt thereof, or a pharmaceutical composition thereof Particular embodiments of the claimed compounds, for example Compound A and Compound B; are described below, in the Examples, and in the claims. Particularly preferred compounds of the invention are Compound A and Compound B.

Additional Embodiments of the invention are described more fully below.

The present invention includes synthetic dimeric cinchona alkaloids having the structure (I, II, III, Compound A, Compound B) shown above, as a cytotoxic compound, useful in pharmaceutical compositions to arrest cell growth and induce apoptosis in cells. The examples below establish synthetic hydroxy-substituted cinchona alkaloids as useful therapeutic agents against cancer.

The invention also provides novel dimeric cinchona alkaloid derivatives having potent activity as cytotoxic agents against cancer cells, including leukemia, prostate cancer, breast cancer and brain cancer cells, and particularly against multi-drug resistant cancer cells, for example, human B-lineage acute lymphoblastic leukemia cells, glioblastoma cells, and BT-20 human breast cancer cells. In addition, specific novel cinchona alkaloid derivatives of the invention are potent inhibitors of tumor clonogenic growth necessary for tumor progression and for tumor cell metastases. While the present invention is not so limited, an appreciation of various aspects of the invention will be gained through the description and the Examples provided below.

Cytotoxic Compounds

As shown in the Examples below, synthetic cinchona alkaloids were tested for cytotoxic activity against cancer cells using both clonogenic assays and apoptosis assays. Compounds A inhibited growth of leukemia, breast, prostate and brain tumor cells, for example as demonstrated in clonogenic assays. with low, nanomolar $IC_{50}$ values. Likewise, Compound A caused apoptotic destruction of cancer cells at nanomolar concentrations.

Useful compounds of the invention are tested for cytotoxicity as described in the Examples below. Such tests include inhibition of clonogenic growth of human cancer cell lines and induction of apoptosis. These assays are well known in the field of cancer therapeutics, and have been well established as effective assays for predicting useful pharmaceutical agents for the treatment of cancer.

In the method of the invention, cancer cells are contacted with approximately nanomolar concentrations of the inhibitory compounds to inhibit cancer cell clonogenic growth.

Prodrug

The term "prodrug" is meant to define a conjugate molecule, where the two molecular species are a hydroxy-substituted cinchona alkaloid derivative and a moiety which renders the conjugate biologically inert, yet which has pharmacological activity upon bioactivation. Prodrugs include, for example, the hydroxy-substituted dimeric cinchona alkaloid derivative compound A covalently attached to molecular species which can be cleaved, for example, enzymatically (i.e., the cleavage of one of the alkyl group or separation of the dimer into monomer, cleavage of an ester group (if present) by esterases) or though acid or base catalyzed hydrolysis. Prodrugs useful in the invention include those that contain, for example, an ester or amide, acyl derivative.

Administration Methods

The compounds in the present invention as well as their conjugates can be formulated as pharmaceutical compositions and administered to a mammalian host, including a human patient in a variety of forms adapted to the chosen route of administration and suitable for administration of the small molecule or its conjugate. The compounds are preferably administered in combination with a pharmaceutically acceptable carrier, and may be combined with or conjugated to specific delivery agents, including targeting antibodies and/or cytokines. It is preferred that the compositions of the present invention be administered parenterally, i.e., intravenously or intraperitoneally, by the infusion or injection. In one embodiment of the invention, the compounds may be administered directly to a tumor by tumor injection; by injecting the compound into the brain, e.g., into ventricular fluid or intratumorally via an intracerebral catheter as per the standard method of convection-enhanced delivery; or by systemic delivery by intravenous or intraarterial injection. The compounds of the invention, including the conjugates, are of a size and composition expected to have ready access to the brain across the blood-brain barrier.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

A concentration of 100 nM to 1 µM was highly effective against human cancer cells in vitro. To achieve this concentration in an adult with 2 L plasma volume, we estimate that 2 micromols of compound A would need to be administered. As the Molecular weight of compound A is 810.1 g, 2 micromol would be 1.6 mg. Therefore, a dose range of 0.1 mg to 10 mg is anticipated to provide effective drug concentrations for compound A and its derivatives pending the evaluation of safety, tolerability and efficacy in human clinical trials. Similar range is anticipated for compound B (molecular weight: 794.1 g) and its derivatives.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compound and their conjugates can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions, or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage.

The liquid carrier or vehicle can be a solvent or liquid dispersion medium comprising, for example, water, ethanol, a polyol such as glycerol, propylene glycol, or liquid polyethylene glycols and the like, vegetable oils, non-toxic glyceryl esters, and suitable mixtures thereof. The proper fluidity can be maintained, for example, by the formation of liposomes, by the maintenance of the required particle size, in the case of dispersion, or by the use of nontoxic surfactants.

The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminium monosterate hydrogels and gelatin.

Sterile injectable solutions are prepared by incorporating the compound or conjugate derivatives in the required amount in the appropriate solvent with various other ingredients as enumerated above and, as required, followed by filer sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligarids expressed on the cells to be treated. The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors. Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When we used in vivo to selectively kill cancer cells or to inhibit cancer cell adhesion/migration, the administered dose is that effective to have the desired effect, e.g., sufficient to reduce or eliminate cancer cells, or sufficient to inhibit adherence/migration of tumor cells. Appropriate amounts can be determined by those skilled in the art, extrapolating using known methods and relationships, from the in vitro data provided in the examples.

In general, the dose of the novel hydroxy-substituted cinchona dimeric alkaloid (A) effective to achieve cancer cell apoptosis, inhibition of cancer cell growth, and increased subject survival time, is that which administers nanomolar amounts of the compound to the cells, preferably 100 nanomolar or greater. The required dose can be lessened by conjugation of the compound to a targeting moiety for example, to preferably 50 nanomolar or greater concentrations or by reducing the target tumor size first by administration of standard radiation therapy or chemotherapy.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the examples.

In general, a dose which delivers about 1-100 mg/kg body weight is expected to be effective, although more or less may be useful. In addition, the compositions of the invention may be administered in combination with other anti-cancer therapies. In such combination therapy, the administered dose of the dimeric alkaloid derivatives would be less than for single drug therapy.

Cancer Treatment

For the purposes of this invention, a method of treating cancer includes contacting cancer cells with a compound of the invention in order to achieve an inhibition of cancer cell growth, a killing of cancer cells, an/or increased patient survival time. Treatment of cancer, by the method of the invention, also includes the prevention of the clonogenic growth of cancer cells, thereby inhibiting metastases.

The cytotoxic and clonogenic growth-inhibiting compound of the invention is suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular hemostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane bleeding, cell volume loss, nuclear condensation, and endonucleolytic degradation of DNA at mucleosome intervals. Loss of plasma membrane integrity is a relatively late event in apoptosis, unlike the form of cell death termed necrosis, which can be caused by hypoxia and exposure to certain toxins and which is typically characterized early-on by increased membrane permeability and cell rupture.

Methods

Medicinal Chemistry. Dihydroquinidine, hydroquinine, quinidine, quinine and cinchonine and other cinchona alkaloid derivatives were purchased from Aldrich Chemical Company and used as such without further purification. $^1$H and $^{13}$C NMR were acquired using a 300 MHz Varian NMR spectrometer equipped with an auto probe assembly. NMR spectra were acquired in $CDCl_3$ at room temperature. Infrared spectra were done in Perkin Elmer 410 portage model instrument using potassium bromide pellets. Mass spectra were taken using a fast atom bombardment mode and high-resolution mass spectra were also acquired to confirm the purity of the materials for biological study. Optical rotation values were obtained from a Polarimeter using sodium lamp line.

Cell lines and Apoptosis Assays. We used the human leukemia cell lines ALL-1 (Ph+ adult ALL, B-lineage), LOUCY (adult T-lineage ALL; ATCC® CRL-2629™), and RAJI (Burkitt's leukemia/lymphoma; ATCC®, CCL-86) as targets to evaluate the anti-leukemic activity of cinchona alkaloids. In vivo leukemia initiating xenograft clones capable of causing disseminated and fatal leukemia in NOD-SCID mice, derived from primary leukemia cells of 5 patients with relapsed ALL, and the aforementioned 3 leukemia cells lines were treated for 24 hours or 48 hours at 37°

C. with cinchona alkaloids at increasing concentrations ranging from 0.5 µM to 50 µM. Controls cells were treated with vehicle (PBS).

Apoptotic death was monitored using multiparameter flow cytometry, as previously reported (Uckun, F. M. et al., British Journal of Haematology, 2011, 153:741-752; Uckun, F. M. et al., J Clin Invest., 2015, 125:1006-18). Controls included vehicle (PBS) treated cells (CON). Cells were analyzed for apoptosis using the standard quantitative flow cytometric apoptosis assay using the Annexin V-FITC Apoptosis Detection Kit from Sigma. The labeled cells were analyzed on a LSR II flow cytometer. The percent apoptosis was calculated using the formula: 100−100×(Percentage of non-apoptotic cells in test sample/Percentage of non-apoptotic cells in untreated control sample). The percentages for Annexin V FITC$^-$PI$^-$ viable cells and Annexin V-FITC$^+$PI$^+$ advanced apoptotic cells for each sample are indicated in the respective quadrants of the depicted two-color fluorescence dot plots.

Confocal Laser Scanning Microscopy. Cells were treated with cinchona alkaloids or PBS in culture medium for 24 hours. After 24 hr of culture, cells were costained with a rabbit polyclonal antitubulin antibody (Green Fluorescence) and the DNA-specific dye Toto-3 (Blue Fluorescence) and examined by laser scanning confocal microscopy using a Bio-Rad MRC-1024 Laser Scanning Confocal Microscope equipped with a Kr/Ar laser (Bio-Rad, Hercules, Calif., USA) mounted on a Nikon Eclipse E800 upright microscope with high numerical aperture objectives (Nikon, Melville, N.Y., USA), as described (Uckun, F. M. et al., *Proc. Natl. Acad. Sci. USA* 2010, 107: 2902-7, 2010; Uckun, F. M. et al., *British Journal of Haematology,* 2010, 149: 508-17; Uckun, F. M. et al., *Blood.* 2013, 121:4348-54).

Clonogenic Assays. The cytotoxicity of cinchona alkaloids was tested against clonogenic human cancer cells was examined using a methylcellulose colony assay system, as described previously (Uckun, F. M. et al., *J. Exp. Med.,* 1986, 163: 347-68; Uckun, F. M. et al., *J. Clin. Invest.,* 1993, 91: 1044-1051). In brief, cells ($10^5$ cells/ml in RPMI-10% fetal bovine serum) were treated for 8 hours at 37° C. with cinchona alkaloids at varying concentrations. After treatment, cells were washed twice, and resuspended in clonogenic medium consisting of RPMI 1640 supplemented with 0.9% methylcellulose, 10% fetal bovine serum, and 50 µM 2-mercaptoethanol. Cells were plated at $5\times10^4$ cells/ml in RPMI 1640 supplemented with 10% fetal bovine serum, and 0.9% methylcellulose in duplicate 35-mm Petri dishes, and cultured for 7 days at 37° C. in a humidified 5% $CO_2$ incubator. Subsequently, cancer cell colonies were enumerated on a grid using an inverted phase-contrast microscope of high optical resolution. Results were expressed as the % Inhibition=[1−(Number of colonies in compound-treated test cultures/Number of colonies in vehicle-treated control cultures)]×100.

EXAMPLES

The invention may be further clarified by reference to the following examples, which serve to exemplify some of the preferred embodiments, and not to limit the invention in any way.

Example 1

Synthesis of Novel Hydroxy-Substituted Dimeric Cinchona Alkaloid Derivatives

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

Quinine was purchased from Aldrich Chemical Company and used as such without further purification. 1H and $^{13}$C NMR were acquired using a 300 MHz Varian NMR spectrometer equipped with an auto probe assembly. NMR spectra were acquired in CDCl$_3$ at room temperature. Infrared spectra were done in Perkin Elmer 410 portage model instrument using potassium bromide pellets. Mass spectra were taken using a fast atom bombardment mode and high-resolution mass spectra were also acquired to confirm the purity of the materials for biological study.

Symmetrical dihydroxy dimeric cinchona alkaloid (Compound A). The synthesis of compound A (2-[6-({4-({5-ethyl-5-hydroxy-1-azabicyclo[2.2.2]octan-2-yl}(6-methoxyquinolin-4yl)methoxy)phthalazine-1-yl}oxy}(6-methoxyquinolin-4yl) methyl)-3hydroxy-1-azabicyclo[2.2.2]octan-3-yl]ethylidyne), the symmetrical hydroxy-substituted dimeric cinchona alkaloid compound is described in Scheme 1. Other synthetic hydroxy substituted dimeric cinchona alkaloid derivatives of Formula I can be synthesized using a modification of this procedure.

Scheme 1

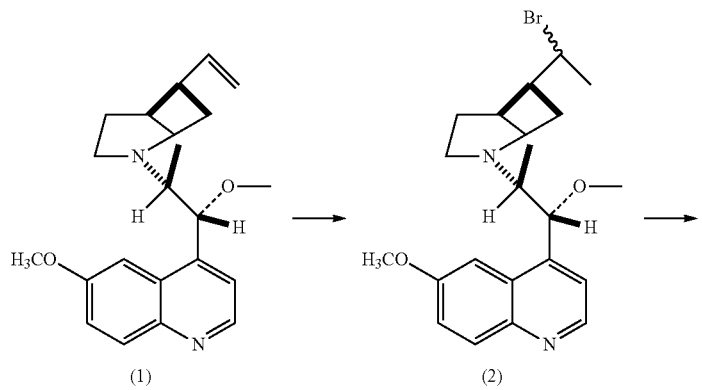

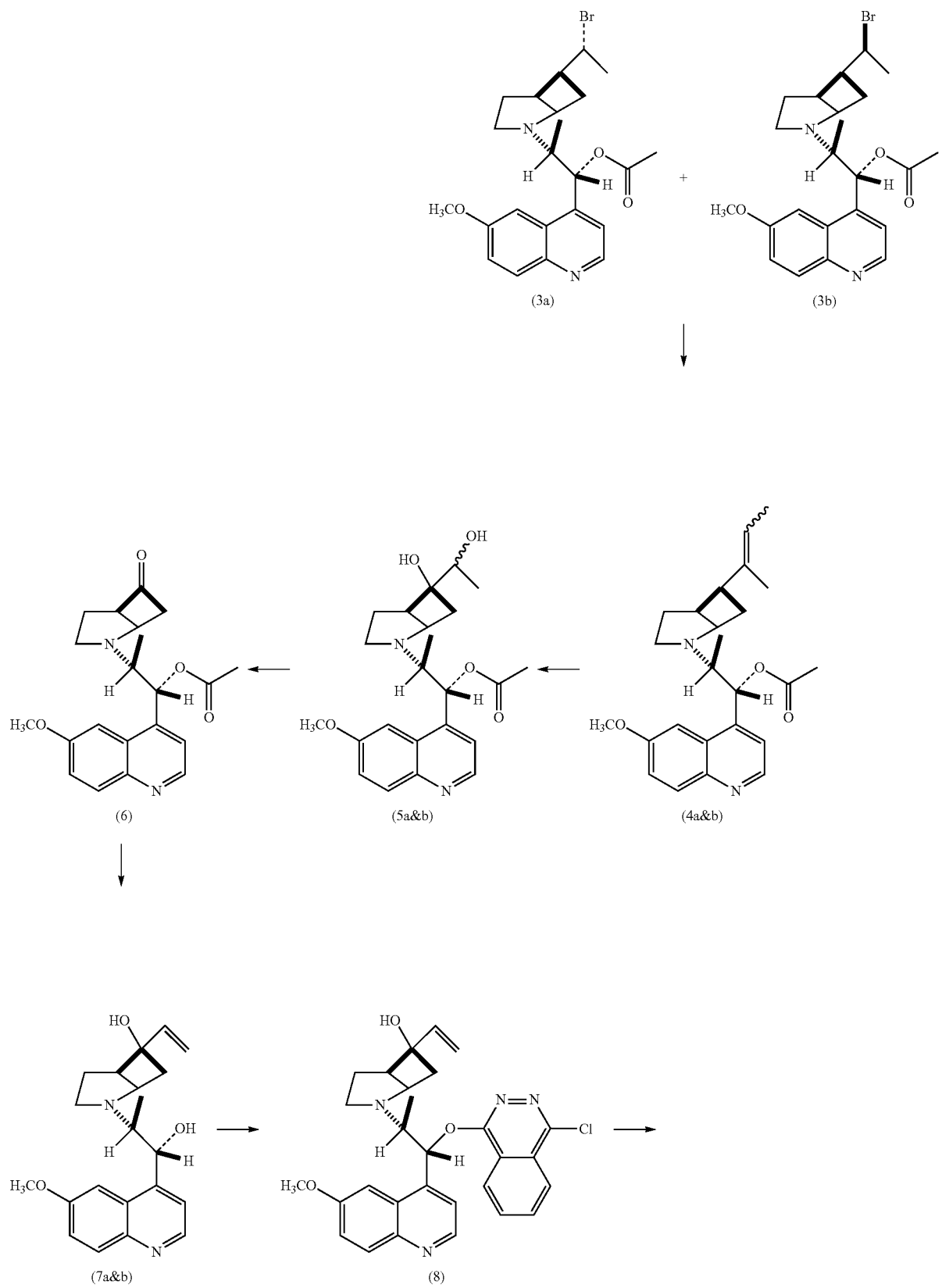

-continued

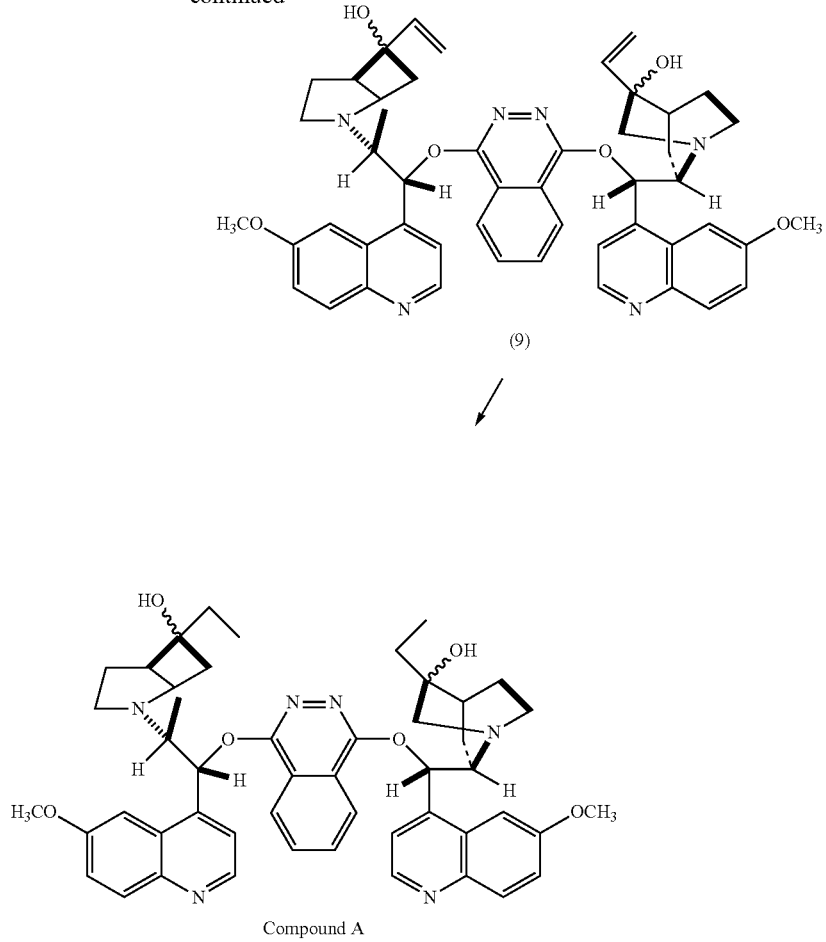

(9)

Compound A

In the initial step, quinine, a commercially available chincona alkaloid, was brominated using hydrobromic acid and hydrobromic acid gas to furnish the brominated derivative (2). In the next step, the hydroxyl group of the alkaloid moiety was protected using an acetate protecting group. Both of the brominated stereoisomers were then subjected to elimination reactions, to furnish compounds (4a) and (4b) respectively. Hydroxylation of the double bond produced compounds (5a) and (5b), which upon stepwise oxidation yielded the required keto compound (6). In the next step, compound (6) was converted into alcohols (7a) and (7b) followed by condensation with the linker 1,4-dichlorophthalazine, which functionalized the hydroxy moiety by eliminating hydrochloric acid and furnished compound (8) as shown in the scheme. Finally, compound (8) was converted into the dimeric hydroxyl alkaloid derivative compound (9) using standard conditions. To obtain the final compound (A), it was necessary to functionalize the double bond in compound (9). To achieve this, compound (9) was reduced with palladium in carbon using a mixture of solvent, such as dichloromethane and ethyl acetate to furnish the final product as a racemic mixture of R and S configuration at the chiral center.

Symmetrical substituted dimeric alkaloid having a ethylene group (54 mg) was dissolved in mixture of ethyl acetate (3 mL) and dichloromethane (3 mL). To this solution was added 10 mg of palladium in carbon and the mixture was stirred under hydrogen using a simple balloon overnight at room temperature. LCMS analysis showed complete conversion of starting material. The mixture was filtered through a celite pad and the filtrate concentrated to yield 40 mg of the final hydroxyl substituted symmetrical dimeric alkaloid. $^1$H NMR (200 MHz, DMSOd6): δ 8.6-8.58 (d, J=4.4 Hz, 2H), 8.48 (m, 2H), 8.25 (m, 2H), 8.0-7.95 (d, J=8.4 Hz, 2H), 7.7-7.4 (m, 6H), 4.9 (m, 2H), 4.05-3.80 (m, 6H), 3.2-2.9 (m, 2H), 2.2-2.0 (m, 6H), 1.8-1.6 (m, 6H), 1.2 (m, 6H), 1.0-0.8 (10H); LCMS (m/z): 811.1 (M+1).

Synthesis of Hydroxy Substituted Dimeric Cinchonine Alkaloid Derivative (Compound B)

In Scheme 2 shown below, we present the synthesis of Compound B ((2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl) methyl)-1-azabicyclo[2.2.2]octan-3-yl] ethylidyne), an unsymmetrical monohydroxy-substituted cinchona alkaloid derivative. Other synthetic hydroxy substituted dimeric cinchona alkaloid derivatives of Formula II can be synthesized using a modification of this procedure.

Scheme 2

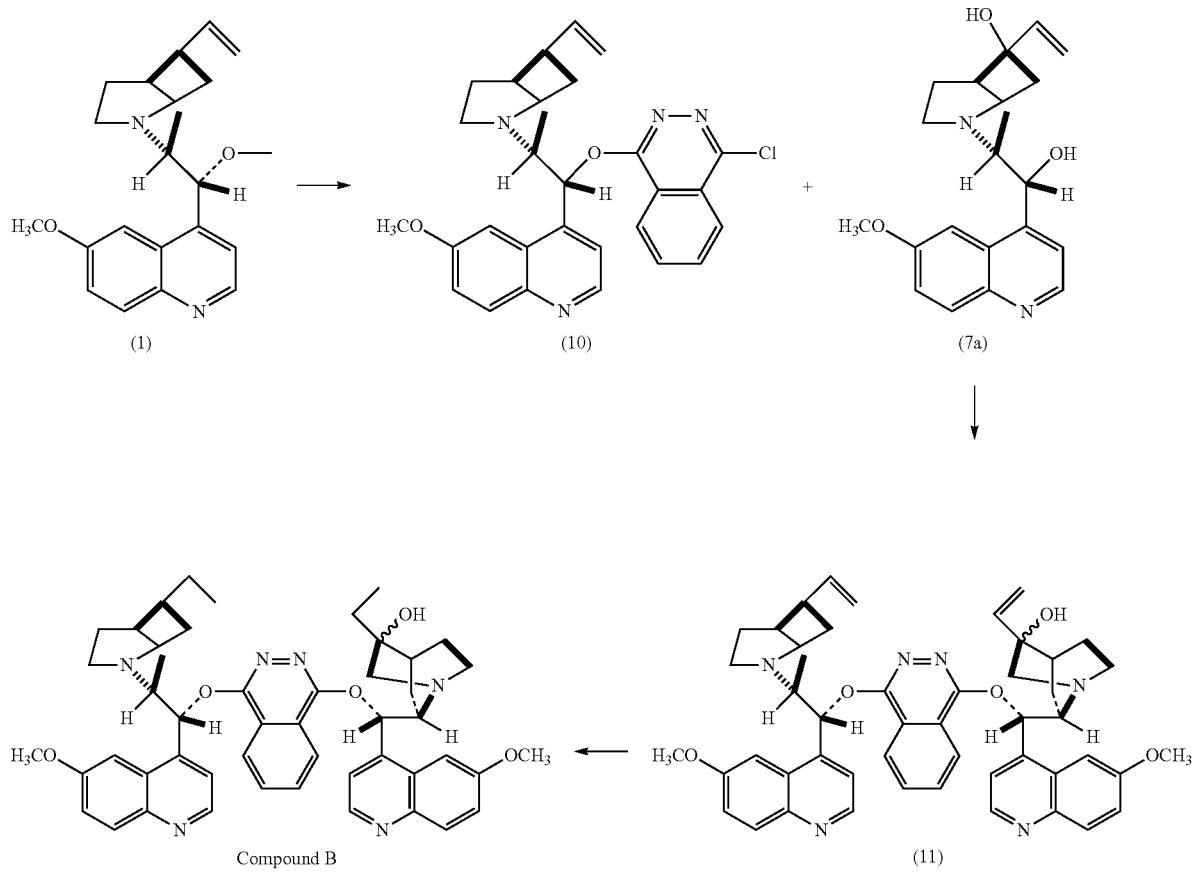

In the above scheme, the first step involves condensation of quinine with the halo-substituted heterocycle 1,4-dichlorophthalazine, to functionalize the hydroxyl group present in the quinine molecule. This was accomplished using an equimolar quantity of the starting material to give a mono-heterocycle substituted cinchonine intermediate derivative (7a) (see scheme 1 for further details) to obtain an unsymmetrically substituted dimeric alkaloid compound (11) which upon reduction with palladium in charcoal furnished the required unsymmetrically hydroxy-substituted dimeric cinchona alkaloid derivative (Compound B)

The unsymmetrical hydroxyl alkaloid derivative (32 mg) was dissolved in a mixture of ethyl acetate (3 mL) and dichloromethane (3 mL). To this solution was added 10 mg of palladium in carbon and the mixture was hydrogenated using hydrogen in a balloon over night at room temperature. LCMS analysis revealed completion of reaction at which time, the mixture was filtered over celite and the filtrate was rotary evaporated to yield 25 mg of the desired unsymmetrical compound. $^1$HNMR (200 MHz, CDCl$_3$): δ 8.65-8.62 (dd, $J_1$=2.2 Hz, $J_2$=2.2 Hz, 2H), 8.35-8.25 (m, 2H), 8.0-7.9 (m, 4H), 7.56-7.53 (t, J=3.4 Hz, 2H), 7.43-7.32 (m, 4H), 6.98-6.96 (d, J=6.2 Hz, 2H), 3.9 (m, 6H), 3.45-3.34 (dd, $J_1$=8.4H, $J_2$=6.4 Hz, 2H), 3.1-3.0 (d, J=13.6 Hz, 1H), 2.9-2.6 (m, 4H), 2.52-2.45 (d, J=14.6 Hz, 1H), 2.0-1.20 (m, 17H), 0.95-0.7 (m, 6H).; LC/mass (m/z): 795.1 (M+1).

Example 2

ARES-BI-C001453 Causes Apoptotic Destruction of Human Leukemia Cells, Including Leukemia-Initiating In Vivo Clonogenic Xenograft Clones Derived from Chemotherapy-Resistant Primary Leukemia Cells of Patients with Relapsed Acute Lymphoblastic Leukemia (ALL)

Methods

We used the human leukemia cell lines ALL-1 (Ph+ adult ALL, B-lineage), LOUCY (adult T-lineage ALL; ATCC® CRL-2629™), and RAJI (Burkitt's leukemia/lymphoma; ATCC®, CCL-86) as targets to evaluate the anti-leukemic activity of ARES-BI-C001453. The ability of anti-cancer drugs to cause apoptosis of leukemia and lymphoma cells derived from patients was shown to be predictive of the effectiveness of the same drugs in clinical settings (F. M. Uckun, et al., 2011, British Journal of Haematology, 153: 741-752). In vivo leukemia initiating xenograft clones capable of causing disseminated and fatal leukemia in NOD-SCID mice, derived from primary leukemia cells of 5 patients with relapsed ALL, and the aforementioned 3 leukemia cells lines were treated for 24 hours or 48 hours at 37° C. with ARES-BI-C001453 at increasing concentrations ranging from 0.5 µM to 50 µM. Controls cells were treated with vehicle (PBS).

Apoptotic death was monitored using multiparameter flow cytometry, as previously reported (Uckun, F. M. et al., British Journal of Haematology, 2011, 153:741-752; Uckun, F. M. et al., J Clin Invest., 2015, 125:1006-18). Controls included vehicle (PBS) treated cells (CON). Cells were analyzed for apoptosis using the standard quantitative flow cytometric apoptosis assay using the Annexin V-FITC Apoptosis Detection Kit from Sigma. The labeled cells were analyzed on a LSR II flow cytometer. The percent apoptosis was calculated using the formula: 100−100×(Percentage of non-apoptotic cells in test sample/Percentage of non-apoptotic cells in untreated control sample). The percentages for Annexin V FITC$^-$PI$^-$ viable cells and Annexin V-FITC$^+$PI$^+$ advanced apoptotic cells for each sample are indicated in the respective quadrants of the depicted two-color fluorescence dot plots.

Results

Figure 2:
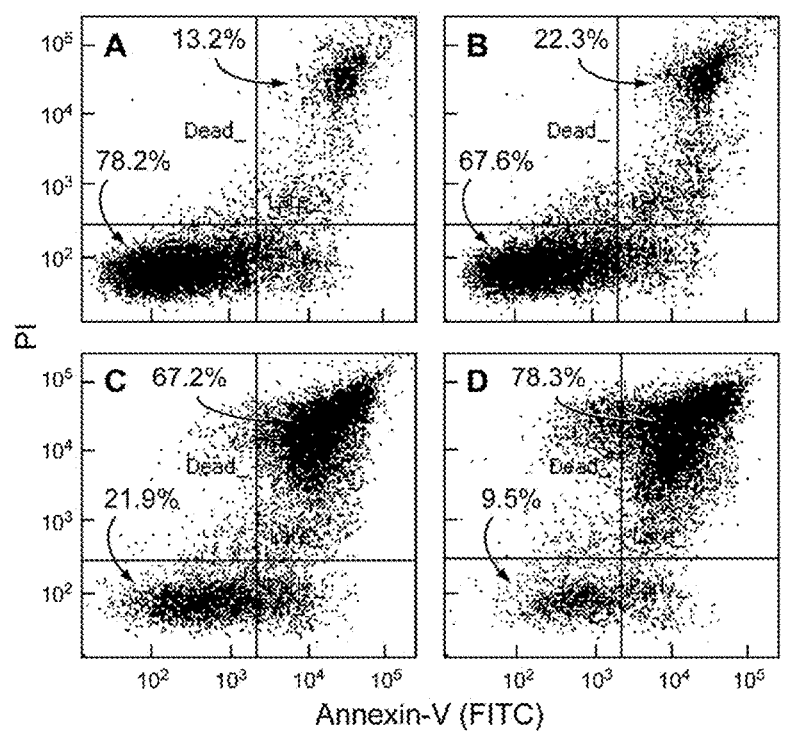
FIG. 2 the flow cytometric evidence for the ability of Compound A (ARES-BI-C001453) to cause apoptotic destruction of in vivo clonogenic, leukemia-initiating primary leukemia cells from B-lineage ALL xenograft clones. After 24 hours of treatment with ARES-BI-C001453 treatment, in vivo clonogenic leukemia cells became apoptotic in a concentration-dependent fashion, as evidenced by the significantly lower percentages of Annexin V-FITC$^-$ PI$^-$ live cells located in the left lower quadrant of the corresponding two-color FACS histogram as well as substantially higher percentage of Annexin V-FITC$^+$ PI$^+$ apoptotic cells located in the right upper quadrant. A: Control cells treated with vehicle (PBS)×24 hours; B: Cells treated with 5 µM ARES-BI-C001453×24 hours; C: Cells treated with 25 µM ARES-BI-C001453×24 hours; D: Cells treated with 50 µM ARES-BI-C001453×24 hours.
Figure 3:
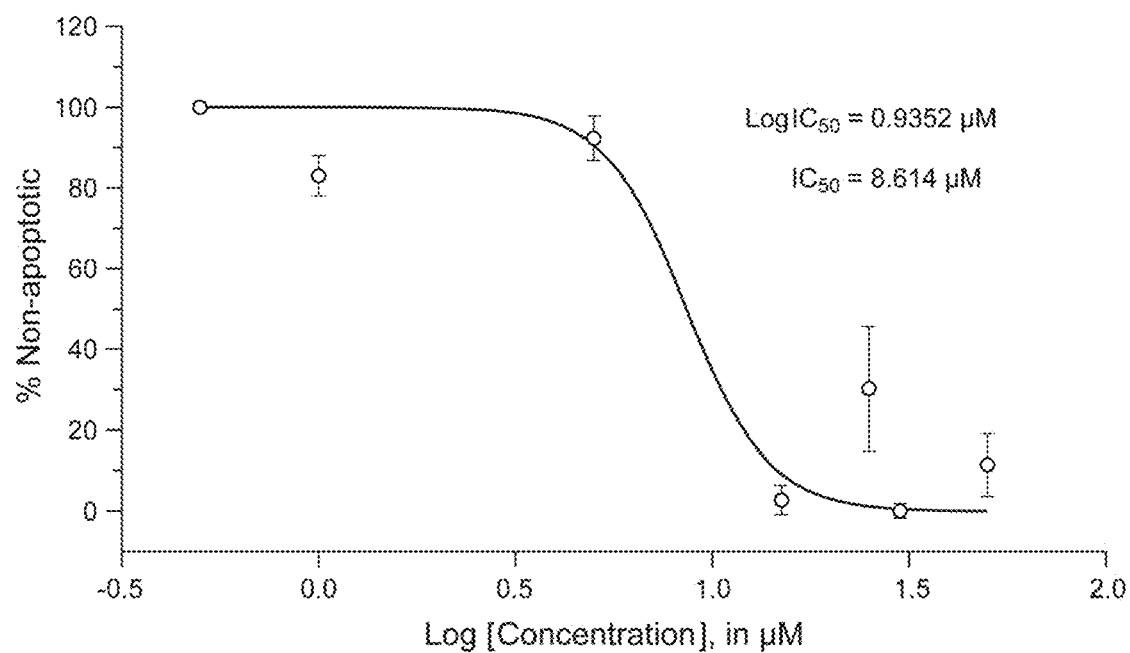
FIG. 3 depicts concentration response curve for the combined dataset from 9 independent experiments in which the anti-leukemic efficacy of Compound A (ARES-BI-C001453) was examined against in vivo clonogenic primary leukemia cells from 5 B-lineage ALL xenograft clones as well as 3 established human ALL cell lines: ALL-1 (Ph+ adult ALL, B-lineage), LOUCY (adult T-lineage ALL; ATCC® CRL-2629™), and RAJI (Burkitt's leukemia/lymphoma; ATCC®, CCL-86). Leukemia cells were treated for either 24 hours (3 experiments) or 48 hours (6 experiments) at 37° C. with ARES-BI-C001453 at increasing concentrations ranging from 0.5 µM to 50 µM. Controls cells were treated with vehicle (PBS). Cells were analyzed for apoptosis as in FIG. 1. Each data point represents the mean±SE values for the % of viable leukemic cells. The depicted graph shows the concentration-dependent reduction in the percentage of residual viable cells in the treated target leukemia cell populations, thereby providing experimental evidence that ARES-BI-C001453 causes apoptotic destruction of human leukemia cells.

ARES-BI-C001453 caused apoptosis in human leukemia cells in a concentration-dependent fashion. The concentration response curve of ARES-BI-C001453 for the combined data sets on leukemia cell lines and xenograft clones are depicted in FIG. 3. The estimated IC$_{50}$ value against xenograft clones derived from primary leukemia cells of 5 patients with relapsed ALL, and the aforementioned 3 leukemia cells lines was 8.6 µM. The anti-leukemic potency of ARES-BI-C001453 against leukemia cells was evidenced by the significantly lower percentages of Annexin V-FITC$^-$PI$^-$ live cells located in the left lower quadrant as well as substantially higher percentage of Annexin V-FITC$^+$PI$^+$ apoptotic cells located in the right upper quadrant of the corresponding two-color fluorescence dot plots (FIG. 1, FIG. 2) which was accompanied by a marked shrinkage and altered SSC in the corresponding FSC/SSC light scatter plot (FIG. 1).

The potency of ARES-BI-C001453 was compared to the potency of ARES-BI-C002453 side by side against LOUCY, ALL-1 and RAJI cell lines. The IC$_{50}$ values were 42 nM, 780 nM, and 8.9 µM, respectively for ARES-BI-C001453. By comparison, ARES-BI-C002453 was less potent than ARES-BI-C001453 with IC$_{50}$ values of 1.5 µM (35.7-fold higher IC$_{50}$ value), 7.3 µM (9.4-fold higher IC$_{50}$ value), and 16.7 µM (1.9-fold higher IC$_{50}$ value), respectively.

Example 3

Compound A (ARES-BI-C001453) Causes Apoptotic Destruction of Human Solid Tumor Cell Lines Methods Confocal Laser Scanning Microscopy. Cells were treated with cinchona alkaloids or PBS in culture medium for 24 hours. After 24 hr of culture, cells were costained with a rabbit polyclonal antitubulin antibody (Green Fluorescence) and the DNA-specific dye Toto-3 (Blue Fluorescence) and examined by laser scanning confocal microscopy using a Bio-Rad MRC-1024 Laser Scanning Confocal Microscope equipped with a Kr/Ar laser (Bio-Rad, Hercules, Calif., USA) mounted on a Nikon Eclipse E800 upright microscope with high numerical aperture objectives (Nikon, Melville, N.Y., USA), as described ((Uckun, F. M. et al., Proc. Natl. Acad. Sci. USA 2010, 107: 2902-7, 2010; Uckun, F. M. et al., British Journal of Haematology, 2010, 149: 508-17; Uckun, F. M. et al., Blood. 2013, 121:4348-54).

Results

Figure 4:
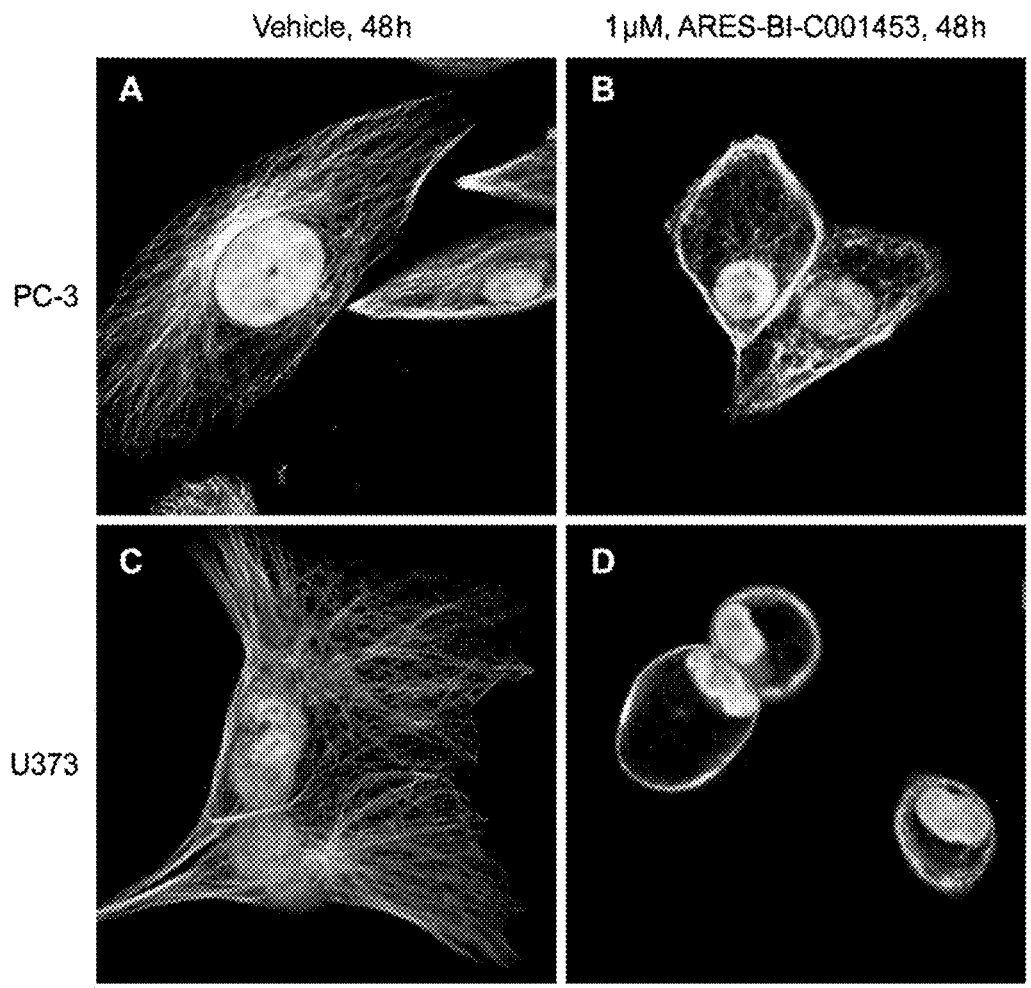
FIG. 4 shows the confocal images of human cancer cells treated with Compound A (ARES-BI-C001453). Cells were treated with 1 µM ARES-BI-C001453 or vehicle (PBS) in FBS-supplemented RPMI for 48 hours and then examined by confocal imaging as described in Materials and Methods. ARES-BI-C001453-treated cells showed signs of advanced apoptosis, including shrinkage and fragmentation of the nuclei, loss of cytoplasmic, and nuclear integrity and loss of the tubulin organization in the cytoplasm and cell membrane.

We evaluated the cytotoxic activity of ARES-BI-C001453 (1 µM) against PC-3 prostate cancer cells and U373 glioblastoma cells using confocal laser scanning microscopy. FIG. 4 depicts the confocal images of PC-3 and U373 cells, respectively, after 48 hours of culture following treatment with 1 µM ARES-BI-C001453 or vehicle (PBS). Whereas PBS-treated control cells maintained their viability, virtually all of the PC-3 or U373 cells treated with ARES-BI-C001453 showed signs of advanced apoptosis, including shrinkage with disruption of microtubules, and fragmentation of the nuclei, loss of cytoplasmic, and nuclear integrity and loss of the tubulin organization in the cytoplasm and cell membrane.

Example 4

Compound A (ARES-BI-C001453) Inhibits Clonogenic Human Tumor Cells with Nanomolar IC$_{50}$ Values.

Methods

Clonogenic Assays. The cytotoxicity of synthetic dimeric cinchona alkaloids was tested against clonogenic human cancer cells was examined using a methylcellulose colony assay system, as described previously (Uckun, F. M. et al., J. Exp. Med., 1986, 163: 347-68; Uckun, F. M. et al., J. Clin. Invest., 1993, 91: 1044-1051). In brief, cells (10$^5$ cells/ml in RPMI-10% fetal bovine serum) were treated for 8 hours at 37° C. with cinchona alkaloids at varying concentrations. After treatment, cells were washed twice, and resuspended in clonogenic medium consisting of RPMI 1640 supplemented with 0.9% methylcellulose, 10% fetal bovine serum, and 50 µM 2-mercaptoethanol. Cells were plated at 5×10$^4$ cells/ml in RPMI 1640 supplemented with 10% fetal bovine serum, and 0.9% methylcellulose in duplicate 35-mm Petri dishes, and cultured for 7 days at 37° C. in a humidified 5% CO$_2$ incubator. Subsequently, cancer cell colonies were enumerated on a grid using an inverted phase-contrast microscope of high optical resolution. Results were expressed as the % Inhibition=[1−(Number of colonies in compound-treated test cultures/Number of colonies in vehicle-treated control cultures)]×100.

TABLE 1

ARES-BI-C001453 Inhibits Clonogenic Cancer Cells

| Cell line | Concentration (µM) | Colonies/5 × 10$^4$ Cells | % Inhibition |
|---|---|---|---|
| BT-20 | 0 | 98.0 (93, 103) | — |
| EXP#1 | 1 | 21.5 (15, 28) | 78.0 |
| | 3 | 10.0 (9, 11) | 89.8 |
| | 10 | 0.0 (0, 0) | >98.9 |
| | C61(10) | 53.0 (45, 61) | 45.9 |
| EXP#2 | 0 | 114.0 (105, 123) | — |
| | 1 | 40.0 (34, 46) | 64.9 |
| | 3 | 9.5 (6, 13) | 91.7 |
| | 10 | 1.0 (1, 1) | 99.1 |
| | C61(10) | 78.0 (73, 83) | 31.6 |
| PC-3 | 0 | 185.5 (175, 196) | — |
| EXP#1 | 1 | 15.0 (11, 19) | 91.9 |
| | 3 | 0.5 (0, 1) | 99.7 |
| | 10 | 1.0 (0, 2) | 99.5 |
| | C61(10) | 41.0 (35, 47) | 77.9 |
| EXP#2 | 0 | 157.5 (145, 170) | — |
| | 1 | 7.0 (5, 9) | 95.6 |
| | 3 | 1 (1, 1) | 99.4 |
| | 10 | 1 (0, 2) | 99.4 |
| | C61(10) | 67.0 (59, 75) | 57.5 |
| ALL-1 | 0 | 323.5 (302, 345) | — |
| EXP#1 | 1 | 27.5 (21, 34) | 91.5 |
| | 3 | 32.0 (28, 36) | 90.1 |
| | 10 | 0.0 (0, 0) | >99.7 |
| | C61(10) | 0.0 (0, 0) | >99.7 |
| EXP#2 | 0 | 226.5 (203, 250) | — |
| | 1 | 99.5 (96, 103) | 56.1 |
| | 3 | 14.5 (11, 18) | 93.6 |
| | 10 | 0.0 (0, 0) | >99.6 |
| | C61(10) | 0.0 (0, 0) | >99.6 |

Results

Figure 5:
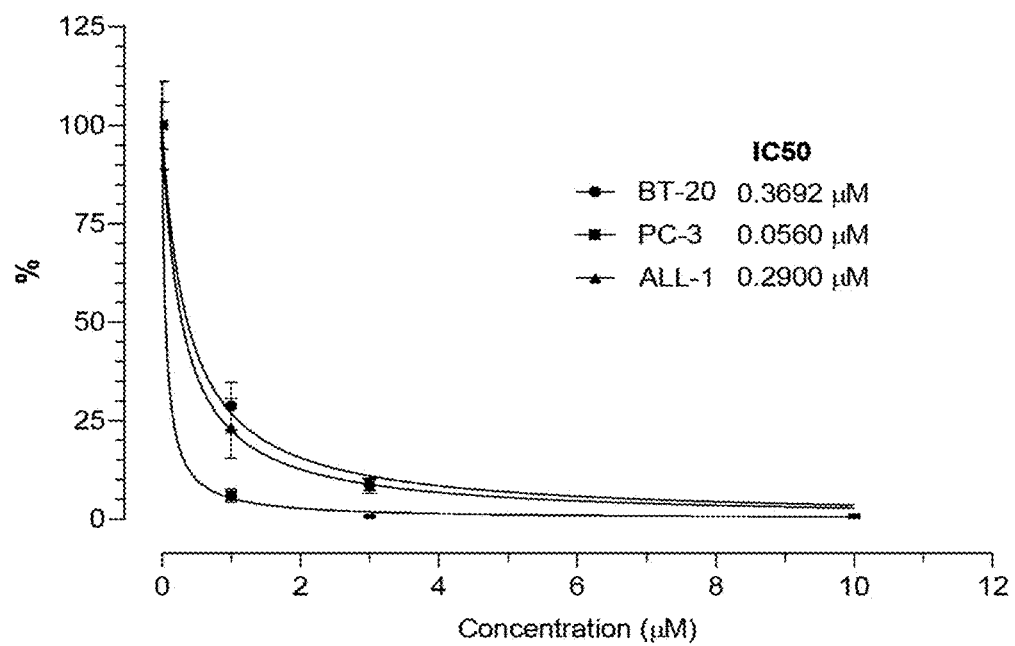
FIG. 5 shows the concentration-response curves for inhibition of the clonogenic growth of human cancer cell lines BT-20 (Triple-negative breast cancer cell line reported in: Chavez, K. J. et al., Breast Dis. 2010; 32(1-2):35-48. doi: 10.3233/BD-2010-0307), PC-3 (prostate cancer cell line reported in; Sahin, T. K. et al., Anti-Cancer Drugs 2020; Feb. 8. doi: 10.1097/CAD.0000000000000910), and ALL-1 (Philadelphia chromosome positive B-lineage ALL cell line reported in: Uckun, F. M. et al., J Clin Invest. 2015 Mar. 2; 125(3):1006-18. doi: 10.1172/JCI76610). The inset lists the estimated IC$_{50}$ values that were extrapolated from the dose-response graphs. The drug concentration that inhibited the clonogenic growth by 50% (IC$_{50}$) was determined by plotting data points from two independent experiments shown in Table 1 over a concentration range and calculating values using non-linear regression analysis of PRISM program. The figure provides experimental evidence that Compound A (ARES-BI-C001453) inhibits human clonogenic tumor cells in a concentration-dependent manner.

ARES-BI-C001453 effectively inhibited the in vitro clonogenic growth of human cancer cell lines in a concentration-dependent fashion and nanomolar $IC_{50}$ values (Table 1, FIG. 5). The $IC_{50}$ values were 369 nM for the triple-negative breast cancer (TNBC) cell line BT-20, 56 nM for the castration-resistant human prostate cancer (CRPC) cell line PC-3, and 290 nM for the BCR-ABL/Ph+ B-lineage ALL cell line ALL-1.

Figure 6:
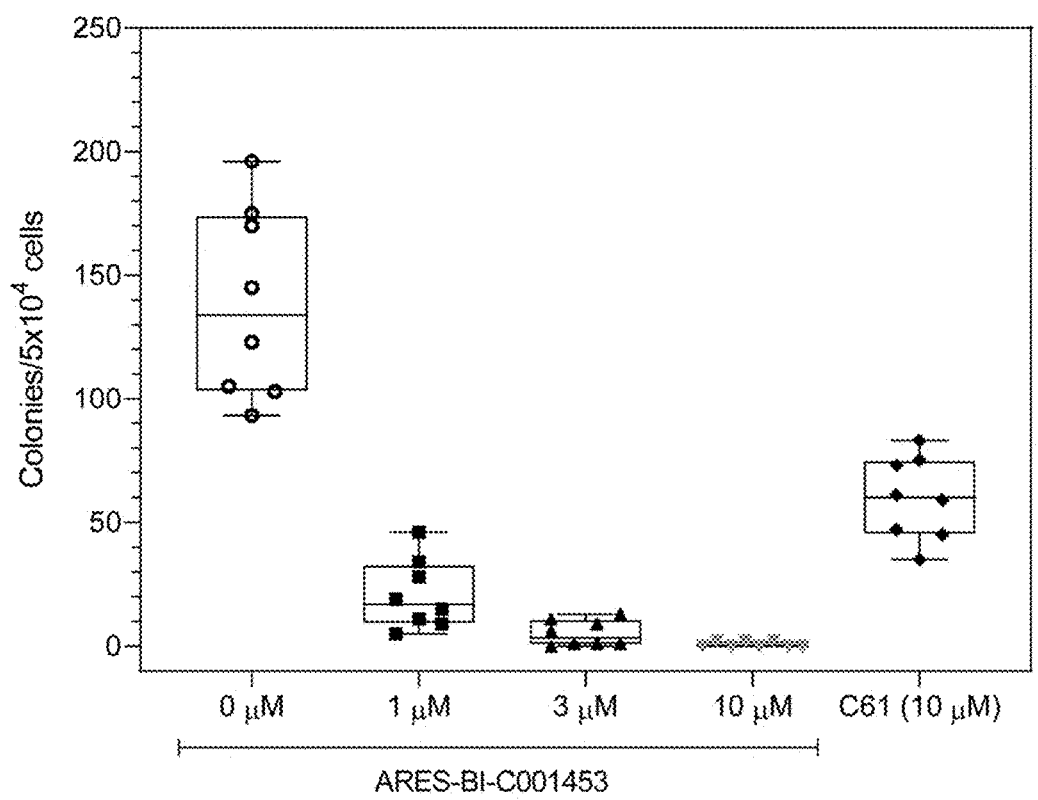
FIG. 6 depicts the Box- and Whisker plots of the number of colonies detected in the cultures of BT-20 or PC-3 cells exposed to increasing concentrations (1, 3, 10 µM) of Compound A (ARES-BI-C001453) or a fixed concentration (10 µM) of the control cinchona alkaloid derivative C61.
Figure 7:
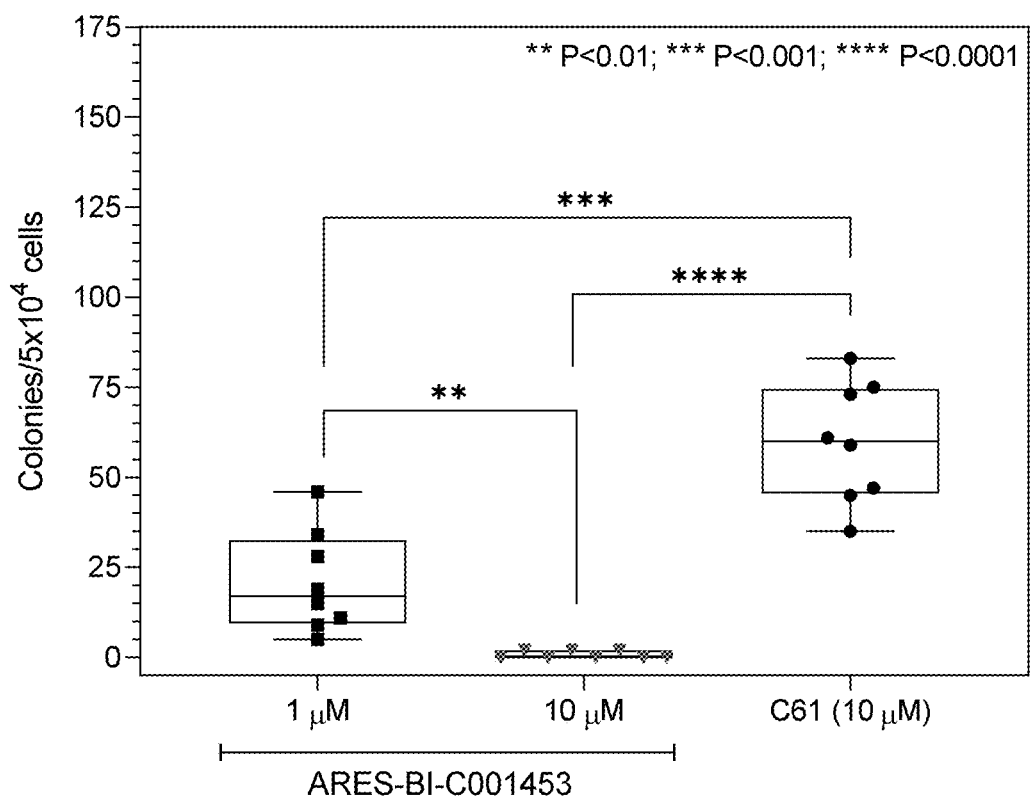
FIG. 7 depicts the Box- and Whisker plots of the number of colonies detected in the cultures of BT-20 or PC-3 cells exposed to 1 µM or 10 µM of ARES-BI-C001453 or 10 µM of the control cinchona alkaloid derivative C61.

While at 10 µM, both ARES-BI-C001453 and C61 abrogated the in vitro colony formation by ALL-1 cells, ARES-BI_C001453 was significantly more potent than C61 against both BT-20 and PC-3 cells (FIG. 1). At 1 µM, ARES-BI-C001453 caused 82.6±8.1% (mean±SE) inhibition of clonogenic growth by these aggressive human cancer cell lines in 4 experiments (2 experiments with PC-3 and 2 experiments with BT-20), whereas C61 caused only 53.2±11.3% inhibition at a 10-fold higher concentration (Table 1). 10 µM ARES-BI-C001453 inhibited the clonogenic growth of BT-20 and PC-3 cells by 99.2±0.2%. The mean number of residual treatment-resistant residual clones forming colonies in cultures exposed to 1 µM ARES-BI-C001453 was $20.9 \pm 5.3/5 \times 10^4$ cells, which was significantly lower than the mean number of residual clones (viz.: $59.8 \pm 6.3/5 \times 10^4$ cells) in cultures treated with C61 at a 10-fold higher concentration (T-test, two-tailed, P=0.0002) (Table 1, FIG. 6, FIG. 7). The differential sensitivity of cancer cells to ARES-BI-C001453 v.s. C61 was most striking for PC3 cells: Whereas the estimated $IC_{50}$ for ARES-BI-C001453 was 129 µM and it caused >99% inhibition at 3 µM, C61 inhibited at 10 µM only 67.7% (Table 1). These results indicate that the ARES-BI-C001453 is substantially more potent against human solid tumor cells than our previously reported lead cinchona alkaloid compound C61.

Abbreviations

H: hydrogen; Me: Methyl; Et: Ethyl; Pr: Propyl; Bu: Butyl; tBu: tertiary butyl; Ph: Phenyl; PhCH2: Benzyl; OH hydroxy; OMe: Methoxy; OEt: ethoxy; OPr: propyl oxy; OBu: Butoxy, OtBu: tertiary butoxy; OPh: phenoxy; $OCH_2Ph$: Benzyl oxy; F: Fluorene; Cl: Chlorine; Br: Bromine; I: Iodine; COOH: Carboxyl; COOMe: methyl carboxy; COOEt: ethyl carboxy
Linker List. Linkers, L, may be chosen from the following list:
1,4-dichlorophthalazine; 2,4-dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-cloro-3,6-dibromopyrimidine; 3,6-dichloro-4-methyl pyridazine; 2,6-difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; 2,4-dichloropyrimidine.

REFERENCES CITED

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

PATENTS

1. P. Boratynski and J. Skarzewski, Polish Potent PL215 451B1 issued on Dec. 31, 2013. Epoxy derivatives of the cinchona alkaloids and process for the preparation of the epoxy derivatives of cinchona alkaloids, 2013.
2. L. Celewicz, K. Kacprzak, P. Ruszkowski, U.S. Pat. No. 9,301,956B2 issued on Apr. 5, 2016, "Application of cinchona alkaloid derivatives as cytotoxic compounds"0.2016. PCT Pub. No.: WO2015/041551, Pub. Date: Mar. 26, 2015
3. L. Celewicz, K. Kacprzak, P. Ruszkowski, Canadian Patent #2891633 issued on Mar. 26, 2015 "Application of Cinchona Alkaloid derivatives as cytotoxic compounds". 2015.
4. P. A. Genne and H. Ibrahim, U.S. Pat. No. 6,528,524 issued Mar. 4, 2003. Pharmaceutical compositions containing cinchonine dichlorohydrate; PCT Pub. No. WO98/56383, PCT Pub. Date: Dec. 17, 1998
5. B. D. Chauffert, P. A. Genne, G. G. Lyon. All of France; Roland-Yves Mauvernay. Lausanne, Switzerland; U.S. Pat. No. 5,635,515 issued Jun. 3, 1997; Therapeutic Agents for the treatment of multidrug resistance of cancers. 1997.
6. M. Padval, P. Elliott, U.S. Pat. No. 112,199 issued on May 26, 2005." Therapeutic Regimens for administering drug combinations"0.2005.
7. I. Yutaka, M. Yasushi, F. Yoshiro, M. Osaka, European Patent #1 477 488A1 issued on Nov. 17, 2004. "Novel Optically active compounds, methods for kinetic optical resolution of carboxylic acid derivatives and catalysts therefor", 2004.

JOURNAL PUBLICATIONS

1. J. A. Baldwin, M. D. McLeod. The Sharpless asymmetric amino dihydroxylation. J. Chem Soc. Perkin Trans. ((2002) 1, 2733-2746.
2. P. J. Boratynski, Dimeric Cinchona alkaloids. Comprehensive Review. Mol Divers (2015). 19, 385-422
3. R. T. Brown and D. Curless, Stereospecific synthesis of erythron cinchona alkaloids from secologanin, Tetrahedron Letters. (1986), 27(49), 6005-6008.
4. K. K. Chavez, S. V. Garimella, S. Lipkowitz. Triple negative breast cancer cell lines: one tool in the search for better treatment of triple negative breast cancer. Breast Dis. (2010), 32(1-2), 35-48. doi:10.3233/BD-2010-0307
5. S. R. Chemler. Phenanthroindolizidines and phenanthroquinolizidines: Promising alkaloids for anti-cancer therapy. Curr Bioact Compd (2009), 5(1), 2-19.
6. Cuendet M, Pezuto J M. Antitumor Alkaloids in Clinical Use or in Clinical Trials. [In] Modern Alkaloids: Structure, Isolation, Synthesis and Biology; (2007) pp. 25-52. Eds.: E. Fattorusso, O. Taglialatela-Scafati. Print ISBN: 9783527315215|Online ISBN:9783527621071|DOI: 10.1002/9783527621071. First published:24 Oct. 2007. Wiley Online Library.
7. C. Fitzmaurice C et al., Global, Regional, and National Cancer Incidence, Mortality, Years of Life Lost, Years Lived With Disability, and Disability-Adjusted Life-Years for 29 Cancer Groups, 1990 to 2017: A Systematic Analysis for the Global Burden of Disease Study. JAMA Oncol. (2019) Sep. 27; 5(12):1749-68. doi: 10.1001/jamaoncol.2019.2996. Online ahead of print, 8. M. Ihara, N. Taniguchi, K. Noguchi, K. Fukumoto," Total synthesis of hydrocinchonidine and hydrocinchonine via photo-oxygenation of an indole derivative", J. Chem. Soc. Perkin Trans. (1988) I, 1277-1281.
9. H. C. Kolb, M. S. Van Nieuwenhze, K. B. Sharpless Catalytic asymmetric dihydroxylation. Chem. Rev. (2004) 94, 2483-2547.
10. A. Lee, F. C. Lee Medical oncology management of advanced hepatocellular carcinoma 2019: a reality check. Front Med. (2020) Jun.; 14(3):273-283. doi: 10.1007/s 11684-019-0728-2. Epub (2019) Dec. 21.
11. S Y Lee, Y H Rhee, S J Jeong, H J Lee," Hydrocinchonine, cinchonine, and quinidine potentiate paclitaxel-induced cytotoxicity and apoptosis via multidrug resistance reversal in MES-SA/DX5 uterine, Environmental Toxicology, (2011) 26, 424-431.
12. A. R. Martirosyan, R Rahim-Bata, A B Freeman," Differentiation-inducing quinolines as experimental breast cancer agents in the MCF-7 human breast cancer cell model" Biochemical Pharmacology, (2004) 68, 1729-1738.
13. N. M. Mattock and W. Peters. "The experimental Chemotherapy of leishmaniasis" Annals of Tropical Medicine and Parasitology, (1975), 69(4), 449-462.
14. D. E. Myers, S. Yiv, S. Qazi, H. Ma, I. Cely, A. Shahidzadeh, M. Arellano, E. Finestone, P. S. Gaynon, A. Termuhlen, J. Cheng, F. M. Uckun F M. CD19-antigen specific nanoscale liposomal formulation of a SYK P-site inhibitor causes apoptotic destruction of human B-precursor leukemia cells. Integr Biol (Camb). (2014) Jul. 21; 6(8):766-80. doi: 10.1039/c4ib00095a. PMID: 24910947 PMCID: PMC4158964
15. H. Rafei, H. M. Kantarjian, E, J. Jabbour. Targeted therapy paves the way for the cure of acute lymphoblastic leukaemia. Br J Haematol. (2020) January; 188(2):207-223. doi: 10.1111/bjh.16207. Epub 2019 Sep. 30. PMID 31566728 Review.
16. K. V. Raju, P. Kharel, R. Pandey, R. Garje, A. B. Chandra, Review of Indications of FDA-Approved Immune Checkpoint Inhibitors per NCCN Guidelines with the Level of Evidence. Cancers (2020), 12(3), 738; https://doi.org/10.3390/cancers12030738
17. Rosenkranz V, Winke. Induction of apoptosis by alkaloids, non-protein amino acids and cardiac glycosides in human promyelocytic HL-60 cells. Z. Naturforsch. (2007) 62c, 458-466.
18. Rosenkranz V, Winke. Alkaloids Induce Programmed Cell Death in Bloodstream Forms of Trypanosomes (*Trypanosoma b. brucei*). Molecules (2008) 13, 2462-2473.
19. S. Schläger, B. Dräger. Exploiting plant alkaloids. Curr Opin Biotechnol (2016) 37, 155-64.
20. T. K. Sahin, O. H. Aktepe., F. M. Uckun, S. Yalcin. Anti-Prostate Cancer Activity of a Nanoformulation of the SYK Tyrosine Kinase Inhibitor C61. Anti-Cancer Drugs (2020) Feb. 8. doi: 10.1097/CAD.0000000000000910. [Epub ahead of print]
21. E Solary, L Mannone, D Moreau, D Caillot," Phase I study of cinchonine, a multidrug resistance reversing agent, combined with the CHVP regimen in relapsed and refractory lymphoproliferative" Lukemia (2000) 14, 2085-2094.
22. H. Tao, L. Zuo L, H. Xu, C. Li, G. Qiao, M. Guo, X. Lin. Alkaloids as Anticancer Agents: A Review of Chinese Patents in Recent 5 Years. Recent Patents on Anticancer Drug Discovery (2020) 15, 2-13.
23. F. M. Uckun S. Qazi, H. Ma, L. Tuel-Ahlgren, Z. Ozer. STAT3 is a substrate of SYK tyrosine kinase in B-lineage leukemia/lymphoma cells exposed to oxidative stress. Proc. Natl. Acad. Sci. USA (2010) 107(7): 2902-7. (PMID. 20133729).
24. F. M. Uckun, R. O. Ek, S. T. Jan, C. L. Chen, S. Qazi. Targeting SYK Kinase-Dependent Anti-Apoptotic Resistance Pathway in B-lineage Acute Lymphoblastic Leukemia (ALL) Cells with a Potent SYK Inhibitory Pentapeptide Mimic. British Journal of Haematology (2010) 149 (4), 508-17.
25. F. M. Uckun, S. Qazi, I. Cely, K. Sahin, A. Shahidzadeh, I. Ozercan, Q. Yin, P. Gaynon, A. Termuhlen, J. Cheng, S. Yiv. Nanoscale liposomal formulation of a SYK P-site inhibitor against B-precursor leukemia. Blood. (2013) May 23; 121(21):4348-54. doi: 10.1182/blood-2012-11-470633. Epub 2013 Apr. 8. PMID: 23568490
26. F. M. Uckun, D. E. Myers, J. Cheng, S. Qazi. Liposomal Nanoparticles of a Spleen Tyrosine Kinase P-Site Inhibitor Amplify the Potency of Low Dose Total Body Irradiation Against Aggressive B-Precursor Leukemia and Yield Superior Survival Outcomes in Mice. EBioMedicine. (2015) Apr. 11; 2(6):554-62. doi: 10.1016/j.ebiom.2015.04.005. eCollection (2015) Jun. PMID: 26285772
27. F. M. Uckun, S. Qazi, Z. Ozer, A. L. Garner, J. Pitt, H. Ma, K. D. Janda. Inducing apoptosis in chemotherapy-resistant B-lineage acute lymphoblastic leukaemia cells by targeting HSPA5, a master regulator of the anti-apoptotic unfolded protein response signalling network. British Journal of Haematology. (2011) 153(6), 741-752
28. F. M. Uckun, D. E. Myers, S. Qazi, Z. Ozer, R. Rose, O. J. D'Cruz, H. Ma. Recombinant human CD19L-sTRAIL effectively targets B cell precursor acute lymphoblastic leukemia. J Clin Invest. (2015) Mar. 2; 125(3):1006-18. doi: 10.1172/JCI76610.
29. F. M. Uckun, K. J. Gajl-Peczalska, J. H. Kersey, L. L. Houston, D. A. Vallera. Use of a novel colony assay to evaluate the cytotoxicity of an immunotoxin containing pokeweed antiviral protein against blast progenitor cells freshly obtained from patients with common B-lineage acute lymphoblastic leukemia. J. Exp. Med. (1986) 163: 347-68.
30. F. M. Uckun, W. Jaszcz, M. Chandan-Langlie, K. G. Waddick, K. Gajl-Peczalska, C. W. Song. Intrinsic radiation resistance of primary clonogenic blasts from children with newly diagnosed B-cell precursor acute lymphoblastic leukemia. J. Clin. Invest. (1993) 91, 1044-1051.
31. F. M. Uckun, S. Qazi, T. Demirer, R. E. Champlin. Contemporary patient-tailored treatment strategies against high risk and relapsed or refractory multiple myeloma. EBioMedicine. (2019) January; 39:612-620. doi: 10.1016/j.ebiom.2018.12.004. Epub (2018) Dec. 10. Review.
32. F. M. Uckun, S. Qazi, L. Hwang, V. N. Trieu. Recurrent or Refractory High-Grade Gliomas Treated by Convection-Enhanced Delivery of a TGFβ2-Targeting RNA Therapeutic: A Post-Hoc Analysis with Long-Term Follow-Up. Cancers (Basel) (2019)1(12). pii: E1892. doi: 10.3390/cancers11121892

The present invention should not be considered limited to the particular examples described above, rather should be understood to cover all aspects of the invention as fairly set out in the attached claims. Various modifications, equivalent processes, as well as numerous structures to which the present invention may be applicable will be readily apparent to those of sill in the art to which the present invention is directed upon review of the instant specification.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A pharmaceutical formulation comprising:
   (a) a compound of Formula I, Compound A, Formula II, Compound B, or Formula III:

I

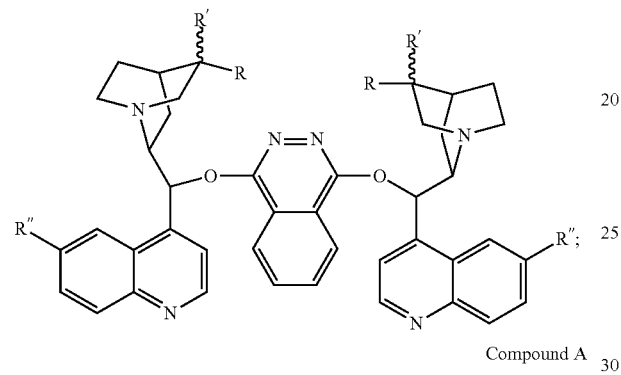

Compound A

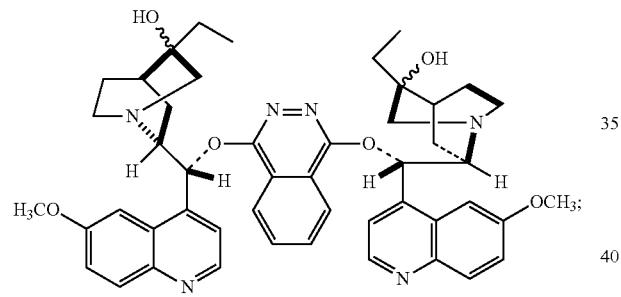

II

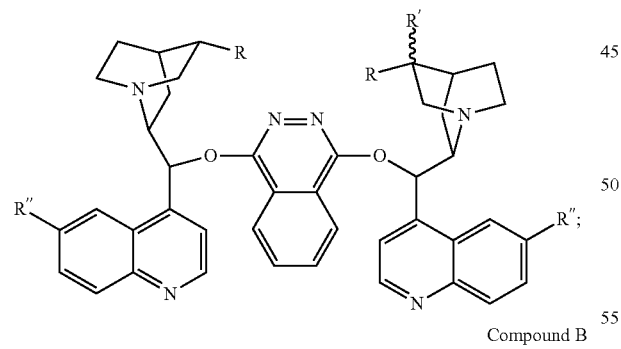

Compound B

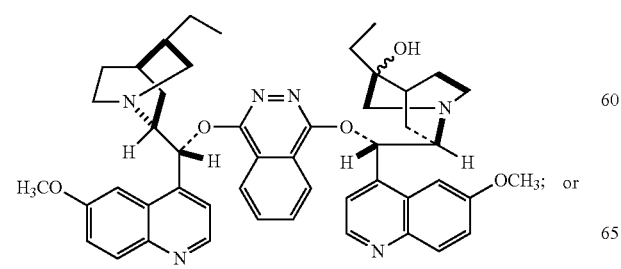

-continued

III

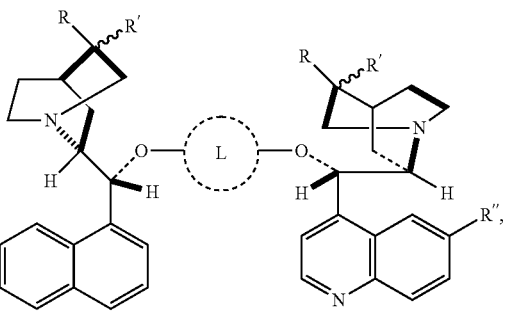

wherein
R is, independent of R' and R", selected from the group consisting of H, Me, Et, Pr, Bu, tBu, Ph, PhCH$_2$, OH, OMe, OEt, OPr, OBu, OtBu, OPh, and OCH$_2$Ph; R' is, independent of R and R", selected from the group consisting of OH, OMe, OEt, OPr, OBu, OtBu, OPh, and OCH$_2$Ph; and R" is, independent of R and R', selected from the group consisting of OMe, OEt, OPh, F, Cl, Br, I, COOH, COOMe, and COOEt;

Compound A is (2-[6-({4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl)methyl)-3hydroxy-1-azabicyclo[2.2.2]octan-3yl]ethylidyne);

Compound B is (2-[6-({4-({5-ethyl-5-hydroxy-1-azabicyclo [2.2.2]octan-2yl}(6-methoxyquinolin-4yl)methoxy)phthalazine-1-yl }oxy}(6-methoxyquinolin-4yl)methyl)-1-azabicyclo[2.2.2]octan-3-yl]ethylidyne);

for the compound of Formula III, the linker moiety L is formed by condensation with 1,4-dichlorophthalazine, 1,4-dicholoroanthraquinone 3,6-dichloropyridazine, 1,4-dichlorophthalazine; 2,4-dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-chloro-3,6-dibromopyrimidine; 3,6-dichloro-4-methyl pyridazine; 2,6-difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; 2,4-dichloropyrimidine; or a substituted heterocyclic derivative of one of:

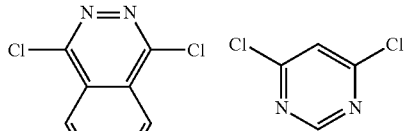

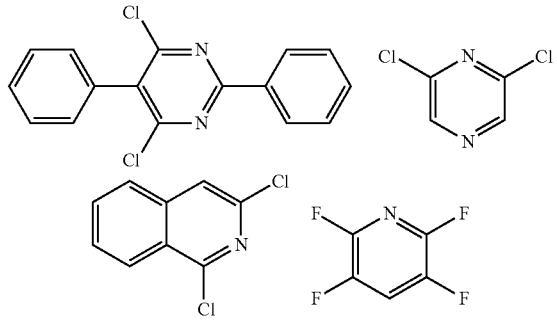

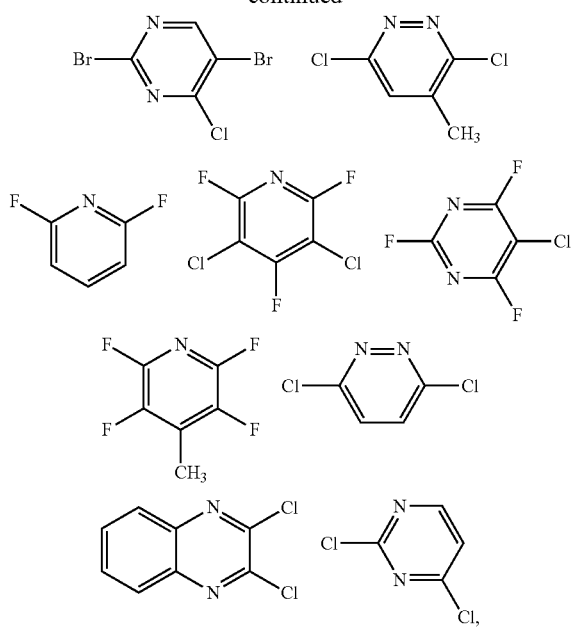

or a pharmaceutically acceptable salt of any of the foregoing: and (b) a pharmaceutically acceptable carrier.

2. The pharmaceutical formulation of claim 1 comprising Compound A.

3. The pharmaceutical formulation of claim 1, wherein the pharmaceutically acceptable carrier comprises one selected from the group consisting of liposomes, fusion proteins, target-specific ligands and monoclonal antibodies.

4. A method for treating cancer in a mammal comprising administering to the mammal in need of said treatment the pharmaceutical formulation of claim 1.

5. The method of claim 4, wherein the mammal is a human cancer patient.

6. The method of claim 5, wherein the human cancer patient is a patient with breast cancer, prostate cancer, glioblastoma multiforme, leukemia, or lymphoma.

7. A method for inducing apoptosis of cancer cells comprising contacting the cancer cells with an effective apoptosis-inducing amount of a compound of Formula I, Compound A, Formula II, Compound B, or Formula III:

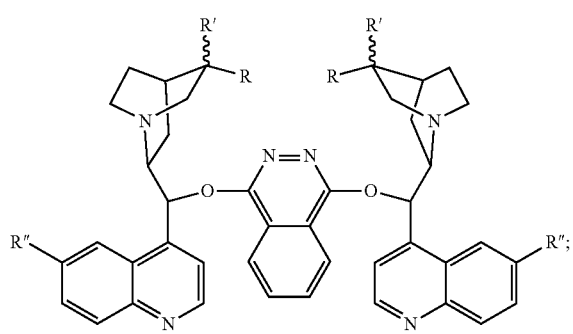

I

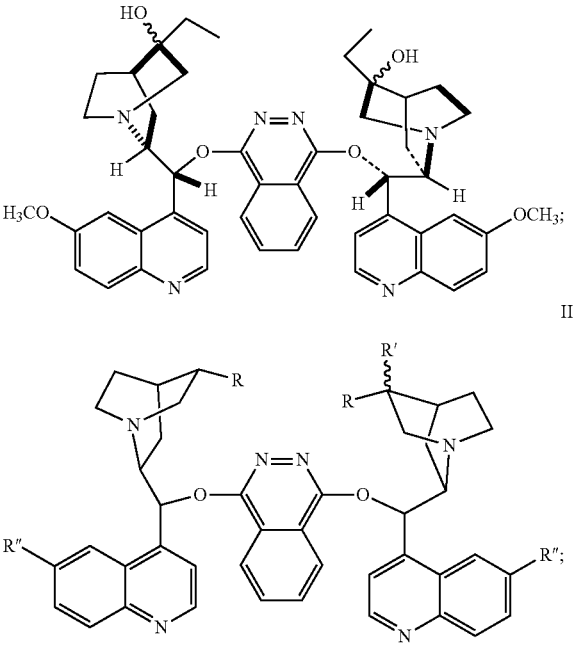

Compound A

II

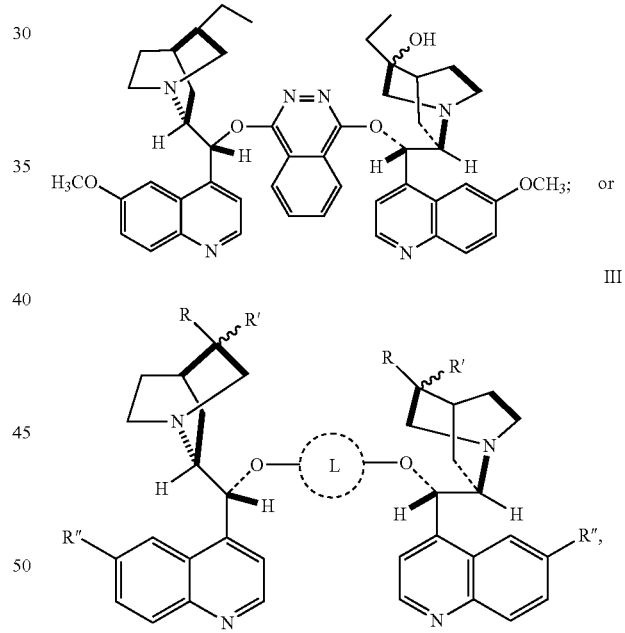

Compound B

III wherein

R is, independent of R' and R", selected from the group consisting of H, Me, Et, Pr, Bu, tBu, Ph, PhCH$_2$, OH, OMe, OEt, OPr, OBu, OtBu, OPh, and OCH$_2$Ph; R' is, independent of R and R", selected from the group consisting of OH, OMe, OEt, OPr, OBu, OtBu, OPh, and OCH$_2$Ph; and R" is, independent of R and R', selected from the group consisting of OMe, OEt, OPh, F, Cl, Br, I, COOH, COOMe, and COOEt;

Compound A is (2-[6-({4-({5-ethyl-5-hydroxy-1-azabicyclo[2.2.2]octan-2yl}(6-methoxyquinolin-4yl)methoxy) phthalazine-1-yl }oxy}(6-methoxyquinolin-4yl) methyl)-3hydroxy-1-azabicyclo[2.2.2]octan-3yl]ethylidyne);

Compound B is (2-[6-([4-({5-ethyl-5-hydroxy-1-azabicyclo[2.2.2]octan-2yl}(6-methoxyquinolin-4yl)methoxy)phthalazine-1-yl}oxy}(6-methoxyquinolin-4yl)methyl)-1-azabicyclo[2.2.2]octan-3-yl]ethylidyne);

for the compound of Formula III, the linker moiety L is formed by condensation with 1,4-dichlorophthalazine, 1,4-dicholoroanthraquinone 3,6-dichloropyridazine, 1,4-dichlorophthalazine; 2,4-dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-chloro-3,6-dibromopyrimidine; 3,6-dichloro-4-methyl pyridazine; 2,6difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; 2,4-dichloropyrimidine; or a substituted heterocyclic derivative of one of:

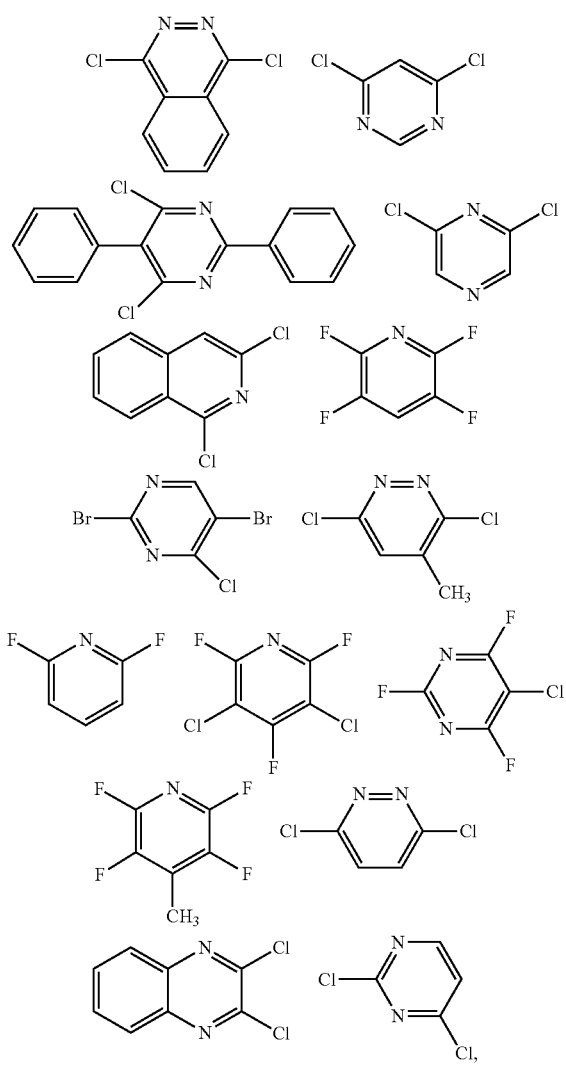

a pharmaceutically acceptable salt thereof, or a pharmaceutical composition thereof.

8. The method of claim 7, wherein the cancer cells are selected from leukemia cells, breast cancer cells, prostate cancer cells, or brain tumor cells.

9. A method for inhibiting the growth of cells comprising contacting the cells with an effective inhibitory dose of a compound of Formula I, Compound A, Formula II, Compound B, or Formula III:

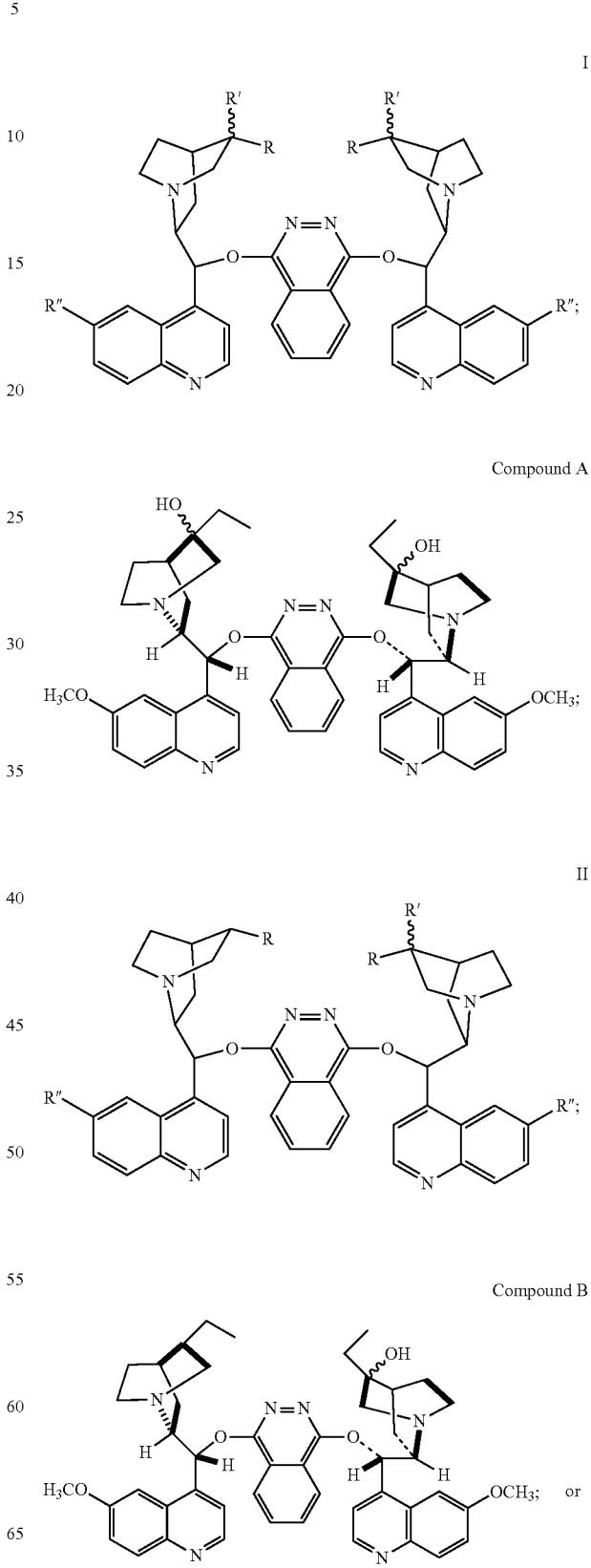

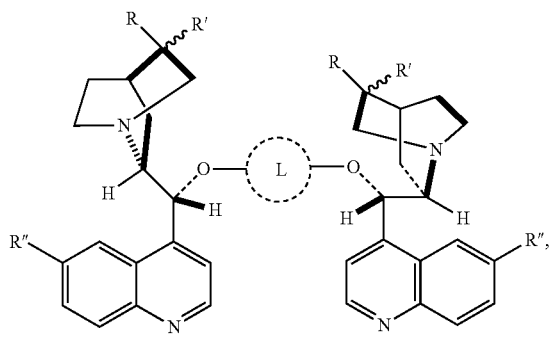

III wherein

R is, independent of R' and R", selected from the group consisting of H, Me, Et, Pr, Bu, tBu, Ph,PhCH$_2$, OH, OMe, OEt, OPr, OBu,OtBu, OPh, and OCH$_2$Ph; R' is, independent of R and R", selected from the group consisting of OH, OMe, OEt, OPr, OBu, OtBu, OPh, and OCH$_2$Ph; and R" is, independent of R and R', selected from the group consisting of OMe, OEt, OPh, F, Cl, Br, I, COOH, COOMe, and COOEt;

Compound A is (2-[6-({4-5-ethyl-5-hydroxy-1-azabicyclo [2.2.2]octan-2yl}(6-methoxyquinolin-4yl) methoxy)phthalazine-1-yl}oxy}(6-methoxyquinolin-4yl)methyl)-3hydroxy-1-azabicyclo [2.2.2]octan-3yl] ethylidyne);

Compound B is (2-[6-({4-({5-ethyl-5-hydroxy-1-azabicyclo [2.2.2]octan-2yl}(6-methoxyquinolin-4yl) methyl)-1-azabicyclo [2.2.2]octan-3-yl]ethylidyne);

for the compound of Formula III, the linker moiety L is formed by condensation with 1,4-dichlorophthalazine, 1,4-dicholoroanthraquinone 3,6-dichloropyridazine, 1,4-dichlorophthalazine; 2,4dichloropyrimidine; 4,6-dichloro-2,5-diphenyl pyrimidine; 2,6-dichloro pyrazine: 1,3-dichloro iso quinoline; 2,3,5,6-tetrafluoro pyridine; 2-chloro-3,6-dibromopyrimidine; 3,6-dichloro-4-methyl pyridazine; 2,6-difluoropyridine; 3,5-dichloro-2,4,6-trifluoro pyridine; 5-chloro-2,4,6-pyrimidine; 2,3,5,6-tetrafluoro-4-methyl pyridine; 3,6-dichloro pyridazine; 2,3-dichloro quinoxaline; 2,4-dichloropyrimidine; or a substituted heterocyclic derivative of one of:

a pharmaceutically acceptable salt thereof, or a pharmaceutical composition thereof.

10. The method of claim 9, wherein the cells are selected from leukemia cells, breast cancer cells, prostate cancer cells, or brain tumor cells.

* * * * *